US010340029B2

(12) United States Patent
Majumdar et al.

(10) Patent No.: US 10,340,029 B2
(45) Date of Patent: Jul. 2, 2019

(54) SYSTEMS AND METHODS FOR THE ANALYSIS OF PROTEIN MELT CURVE DATA

(71) Applicant: LIFE TECHNOLOGIES CORPORATION, Carlsbad, CA (US)

(72) Inventors: Nivedita Sumi Majumdar, San Bruno, CA (US); Harrison Leong, San Francisco, CA (US); Ruoyun Wu, Singapore (SG)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/144,369

(22) Filed: May 2, 2016

(65) Prior Publication Data

US 2016/0321398 A1 Nov. 3, 2016

Related U.S. Application Data

(63) Continuation of application No. 13/364,276, filed on Feb. 1, 2012, now abandoned.

(Continued)

(51) Int. Cl.
*G06T 11/20* (2006.01)
*G16B 40/00* (2019.01)
(Continued)

(52) U.S. Cl.
CPC ........... *G16B 45/00* (2019.02); *G06F 3/0482* (2013.01); *G06F 3/04847* (2013.01);
(Continued)

(58) Field of Classification Search
None
See application file for complete search history.

(56) References Cited

U.S. PATENT DOCUMENTS

2009/0222503 A1* 9/2009 Palais .................. C12Q 1/6816 708/277
2010/0076690 A1* 3/2010 Reja ........................ G06F 19/24 702/19

FOREIGN PATENT DOCUMENTS

EP 2241990 A1 10/2010
JP 2009-508530 5/2009
(Continued)

OTHER PUBLICATIONS

Mahajan, Sumeet, et al. "SERS-melting: a new method for discriminating mutations in DNA sequences." Journal of the American Chemical Society130.46 (2008): 15589-15601.*

(Continued)

*Primary Examiner* — Jason A Pringle-Parker
(74) *Attorney, Agent, or Firm* — Jones Robb, PLLC

(57) ABSTRACT

The present teachings relate to embodiments of systems and methods for the analysis of melt curve data for a plurality of samples. According to various embodiments, a melting temperature ($T_m$) may be determined across a range of different types of protein melt curve data, having variability over a plurality of analytical attributes in order to accommodate the complexity of protein melt curve data. The combination of a plurality of samples, coupled with the complexity of the data gives rise for a need to process the data in a manner that readily facilitates end-user to analysis of the data. Various embodiments of an interactive graphical user interface (GUI) according to the present teachings provide for rapid and sequential changes that may be made by an end user to displayed protein melt curve data to allow such analysis.

18 Claims, 31 Drawing Sheets

Related U.S. Application Data

(60) Provisional application No. 61/438,621, filed on Feb. 1, 2011, provisional application No. 61/450,306, filed on Mar. 8, 2011, provisional application No. 61/496,980, filed on Jun. 14, 2011.

(51) Int. Cl.
*G16B 45/00* (2019.01)
*G06F 3/0482* (2013.01)
*G06F 3/0484* (2013.01)

(52) U.S. Cl.
CPC ........ *G06T 11/206* (2013.01); *G06T 2200/24* (2013.01); *G16B 40/00* (2019.02)

(56) References Cited

FOREIGN PATENT DOCUMENTS

| | | | |
|---|---|---|---|
| JP | 2011-528035 | | 11/2011 |
| JP | 2012-502634 | | 2/2012 |
| JP | 2012-526560 | | 11/2012 |
| WO | 2010/008690 | A1 | 1/2010 |
| WO | 2010/132813 | A2 | 11/2010 |

OTHER PUBLICATIONS

SAS Institute Inc. 2009. JMP 9 Basic Analysis and Graphing. Cary, NC: SAS Institute Inc ("SAS").*

LightCycler 480 as evidenced by Manual, Instruction. "LightCycler 480 Instrument Operator's Manual Software Version 1.5" Roche Applied Science: 2008 ("LightCycler").*

"SERS-Melting: a new method for discriminating mutations in DNA sequences," Journal of the American Chemical Society, 2008, pp. 15589-15601, Mahajan, Sumeet, et al.

"LightCycler 480 Instrument Operator's Manual," 2008, pp. 1-395, ROCHE.

"JMP Release 9—Basic Analysis and Graphing," SAS Institute Inc., Chapter 5, 2009, pp. 143-146, SAS Institute Inc.

"JMP Version 9.0.2," Chapter 5, 2010, pp. 143-154, SAS Institute Inc.

Written Opinion of the ISA issued in International application No. PCT/US2012/023556, dated Jan. 8, 2013.

European Communication pursuant to Article 94(3) EPC in Application No. 12 707 407.8-1952, dated Jun. 26, 2017.

* cited by examiner

| Icon | Flag | Description |
|---|---|---|
| RFU | High Background | Excessive low temperature fluorescence relative to maximum fluorescence gain among the analysis group. |
| NPC | High NPC | Excessive fluorescence gain in NPC relative to maximum fluorescence gain among the analysis group. |
|  | Algorithm Failure | Failure to determine Tm for unknown reasons. |
| Fit? | Sparse Data | Insufficient data available to properly constrain the Boltzmann function fit. |
| RFU | Low Signal | Low fluorescence gain relative to maximum fluorescence gain among the analysis group. |
| Fit | Poor Fit | Poor Boltzmann function fit to the data (high chi-square). |
| RPL | Replicate Mismatch | Number of melt phases differs among replicates. |
|  | Multiple Melts | More than one melt phase was detected. |
| REF | Reference Mismatch | Number of melt phases differs between the sample and reference wells. |

FIG. 19

| # | Protein | Buffer | Salt | Task | Analysis Group |
|---|---|---|---|---|---|
| 7 | YraM | Buffer D | 150 mM NaCl | S | P1 |
| 8 | YraM | Buffer D | 150 mM NaCl | S | P2 |
| 9 | YraM | Buffer C | 50 mM NaCl | S | P1 |
| 10 | YraM | Buffer C | 50 mM NaCl | S | P2 |
| 11 | YraM | Buffer C | 0 mM NaCl | S | P1 |

| # | Well | TM - B | ΔTm - B | Fit | Δ |
|---|---|---|---|---|---|
| 1 | E01 | 54.97 | | 1.49 | 1 |
| 2 | E01 | 55.06 | | 1.50 | 0 |
| 3 | E02 | 55.96 | | 1.47 | 1 |
| 4 | E02 | 56.18 | | 1.52 | 0 |
| 5 | E05 | 54.68 | | 1.42 | 1 |

1610

| # | Hits B | Protein | Task | Analysis Group | ΔTm B |
|---|---|---|---|---|---|
| 3 | | D | S | AG 1 | |
| 4 | | T | S | AG 1 | |
| 5 | | Q | S | AG 1 | |

| # | Well | TM B | ΔTm B | B Fit | Tm B Start | Tm B End | | Sing |
|---|---|---|---|---|---|---|---|---|
| 1 | A01 | 44.02 | -0.73 | 1.44 | 33.85 | 50.74 | 1 | Single |
| 2 | B02 | 44.36 | -0.39 | 1.41 | 34.25 | 51.14 | 1 | Single |
| 3 | C02 | 44.48 | -0.27 | 1.52 | 33.04 | 51.14 | 2 | Single |

SYSTEMS AND METHODS FOR THE ANALYSIS OF PROTEIN MELT CURVE DATA

CROSS-REFERENCE TO RELATED APPLICATIONS

This application is a continuation of U.S. patent application Ser. No. 13/364,276, filed Feb. 1, 2012, which claims priority to U.S. Provisional Patent Application No. 61/438,621, filed Feb. 1, 2011, U.S. Provisional Patent Application No. 61/450,306, filed Mar. 8, 2011, and U.S. Provisional Patent Application No. 61/496,980, filed Jun. 14, 2011, all of which are incorporated herein by reference.

BACKGROUND

As one of ordinary skill in the art of protein chemistry may be apprised, protein melting curve data may vary considerably, and may display variability over a plurality of analytical attributes. Such analytical attributes may include, for example, but not limited by, curve shape, background signal, change in signal amplitude, and noise.

Systems and methods according to the present teachings for the analysis of a protein melt curve data, in which a melting temperature ($T_m$) may be determined, address the need for objective and consistent analysis of protein melt curve data. For protein melt curve data, for example, in high throughput analyses, a plurality of protein samples may be processed, which may create a set of protein melt curve data displaying high variability over a range of analytical attributes.

The combination of a plurality of samples processed simultaneously, coupled with the complexity of the data gives rise for a need to process the data in a manner that readily facilitates end-user evaluation of the data.

BRIEF DESCRIPTION OF THE DRAWINGS

FIG. 19 depicts chart according to various embodiment of systems and methods of an interactive GUI according to the present teachings, which depicts various conditions for which an end user may receive a flag notification.

DETAILED DESCRIPTION

Figure 1:
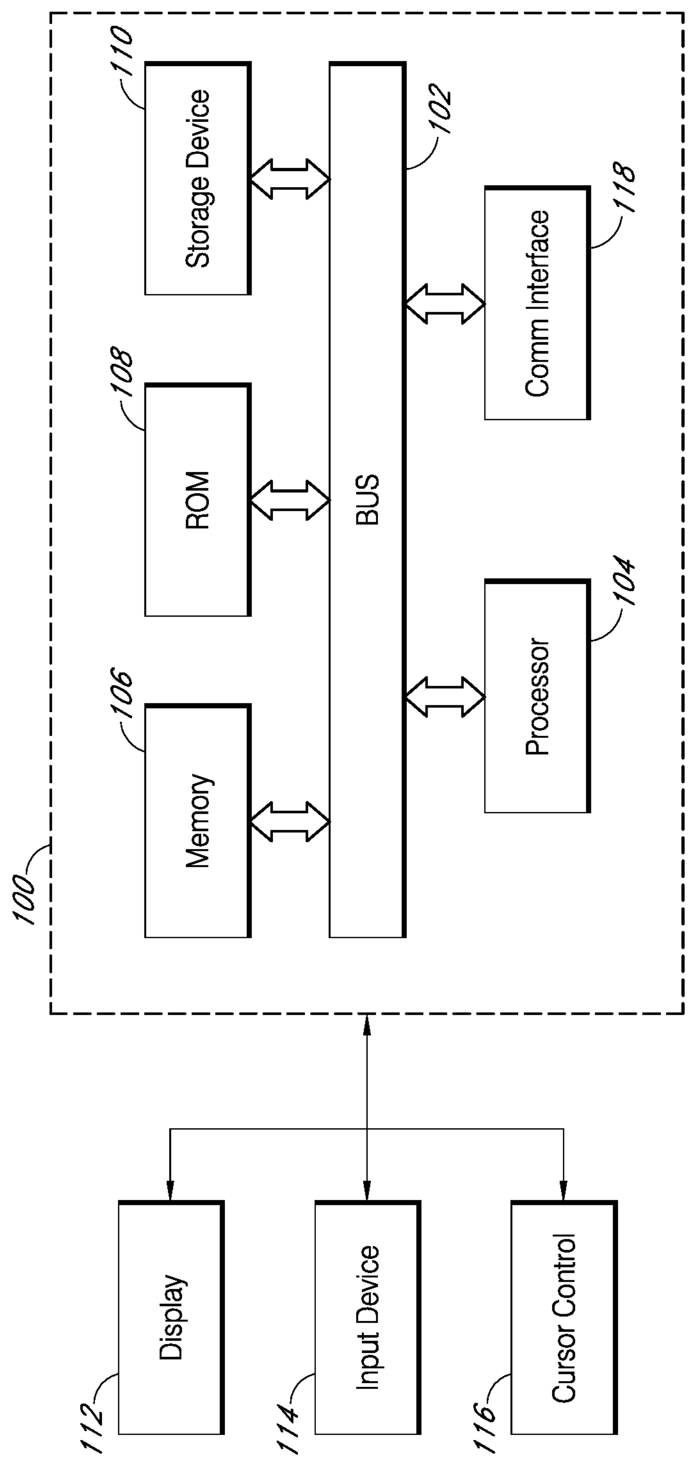
FIG. 1 is a block diagram that illustrates components of an exemplary computer system that may be utilized in the control and interface of a system used for processing protein samples for melt curve analysis.

The present teachings relate to embodiments of systems and methods that readily facilitate end-user analysis of protein melt curve data. According to various embodiments, a melting temperature ($T_m$) may be determined from a protein thermal stability study across a range of different types of protein melt curve data, having variability over a plurality of analytical attributes. For various embodiments, analytical attributes may include, for example, but not limited by, curve shape, background signal, change in signal amplitude, and noise. Additionally, a plurality of samples may be processed under a variety of experimental conditions, thereby creating a substantial amount of data for which an end user may evaluate. For various embodiments, given the complexity and amount of data generated, systems and methods of the present teachings provide ready facilitation of end-user analysis and evaluation of the data. According to various embodiments, an interactive graphical user interface (GUI) is provided to facilitate end-user analysis and evaluation of the data. In various embodiments, an interactive GUI may be an interactive tool providing various features that allow an end user to sequentially and rapidly analyze protein melt curve data. According to various embodiments, an interactive GUI may allow an end user to sequentially and rapidly analyze and evaluate protein melt curve data and subsets of data for the determination of a $T_m$. For various embodiments, an interactive GUI may allow an end user to sequentially and rapidly analyze and evaluate protein melt curve data and subsets of data with respect to the replicate group data, such as the impact of variety of experimental variables on the replicate data sets, as well as the central tendency and variance of replicates associated with a selected set of protein melt curve data.

One of ordinary skill in the art may recognize various assays utilizing the determination of the melting temperature ($T_m$) of a protein. The process in which a protein having, for example, a tertiary structure, goes from that tertiary structure to a random coil structure is referred to in the art as, for example, but not limited by, protein denaturation, protein unfolding, and protein melt. Additionally, a protein under various sample solution conditions may show a variation or shift in the observed $T_m$ for that protein as a function of the sample solution conditions. Various terms such as thermal melt assays (TMA), thermal shift assay (TSA), protein thermal shift (PTS) analysis, and differential scanning fluorimetry (DSF) are examples of terms of the art in which the determination of the $T_m$ of a protein or proteins is central to the analysis.

With respect to aspects of measurement science applied to protein chemistry, a change in detector signal amplitude may be observed as a function of the change in the folded state of a protein. In that regard, various analyses may be based on either the increase or decrease of fluorescence signal amplitude as it varies with respect to change in temperature applied to a protein sample.

For example, in various analyses, the signal amplitude may arise from an amino acid residue of the protein, such as tryptophan. As one of ordinary skill in the art is apprised, the intensity, quantum yield, and wavelength of maximum fluorescence emission of tryptophan are very solvent dependent. The fluorescence spectrum shifts to shorter wavelength and the intensity of the fluorescence increases as the polarity of the solvent surrounding the tryptophan residue decreases. Therefore, as a protein unfolds, buried tryptophan residues may be exposed to a more polar aqueous solvent environment, so that a decreasing signal amplitude may be observed from a folded to an unfolded state.

Instead of using an intrinsic signal arising from a protein molecule, other analyses may utilize a dye to indicate a folded state of a protein. For example, a fluorescence dye, such as Sypro®Orange, may be utilized to monitor the folded state of a protein. For Sypro®Orange in a polar solvent environment, quenching of the fluorescent signal is observed. For Sypro®Orange associated with the surface groups of a folded protein in solution, the dye is in an aqueous environment, so that its fluorescence signal is quenched. As a protein is unfolded, using for example, thermal unfolding, hydrophobic regions or residues may be exposed. Sypro®Orange may then bind to hydrophobic regions or residues, and fluorescence may thereby be increased. For such a Sypro®Orange assay, then an increasing signal amplitude going from a folded to unfolded state may be observed. Dyes, such as 1-anilinonaphthalene-8-sulfonic acid (1,8-ANS) and 4,4'-Dianilino-1,1'-Binaphthyl-5,5'-Disulfonic Acid (Bis-ANS), which are quenched in aqueous environments, have been shown to be useful for monitoring protein folding, in which the fluorescence of 1,8 ANS and Bis-ANS may increase substantially in the process of, for example, protein refolding.

As one of ordinary skill in the art of protein sciences is apprised, monitoring protein thermal stability may be done in both academe, as well as industry for a variety reasons. For example, but not limited by, protein melt curve studies, or thermal studies, may be done for investigation of mutations to a target protein as a result of, for example, site directed mutagenesis studies. Additionally, protein thermal stability studies may be done to screen for the impact on protein stability due to a variety in vitro processing and storage conditions. Such protein thermal stability studies may screen for the impact that a variety of additives, such as, buffers, ligands, and organic agents may have on the thermal stability of the protein of interest. High throughput screening of the binding of drug candidates to protein targets may also be monitored by the impact that the binding of a drug candidate may have on protein thermal stability. Accordingly, identifying the conditions that affect protein thermal stability may enhance the identification of a variety of desired conditions impacting protein purification, crystallization, and functional characterization.

As will be discussed in more detail subsequently, various embodiments of systems and methods may utilize detector signal data collected over the entirety of a defined temperature range for a protein melt assay. Such signals may be stored in a variety of computer readable media. In various embodiments according to the present teachings, a computer program product may be provided, which may include a tangible computer-readable storage medium whose contents include a program with instructions that when executed on a processor perform a method for providing an end user with the ability to sequentially and rapidly analyze and evaluate protein melt curve data.

FIG. 1 is a block diagram that illustrates a computer system 100 that may be employed to carry out processing functionality, according to various embodiments, upon which embodiments of the present teachings may be implemented. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 100 may include bus 102 or other communication mechanism for communicating information, and processor 104 coupled with bus 102 for processing information.

Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) are provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, and/or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, and the like. Software and data transferred via communications interface 118 are in the form of signals which can be electronic, electromagnetic, optical or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be in communication through communications interface 118 to a display 112, such as a cathode ray tube (CRT), liquid crystal display (LCD), and light-emitting diode (LED) display for displaying information to a computer user. In various embodiments, computing system 100 may be couple to a display through a bus. An input device 114, including alphanumeric and other keys, is coupled to bus 102 for communicating information and command selections to processor 104, for example. An input device may also be a display, such as an LCD display, configured with touch screen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution. Such instructions, generally referred to as "computer program code" (which may be grouped in the form of computer programs or other groupings), when executed, enable the computing system 100 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including connectivity to bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

It will be appreciated that, for clarity, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Figure 2:
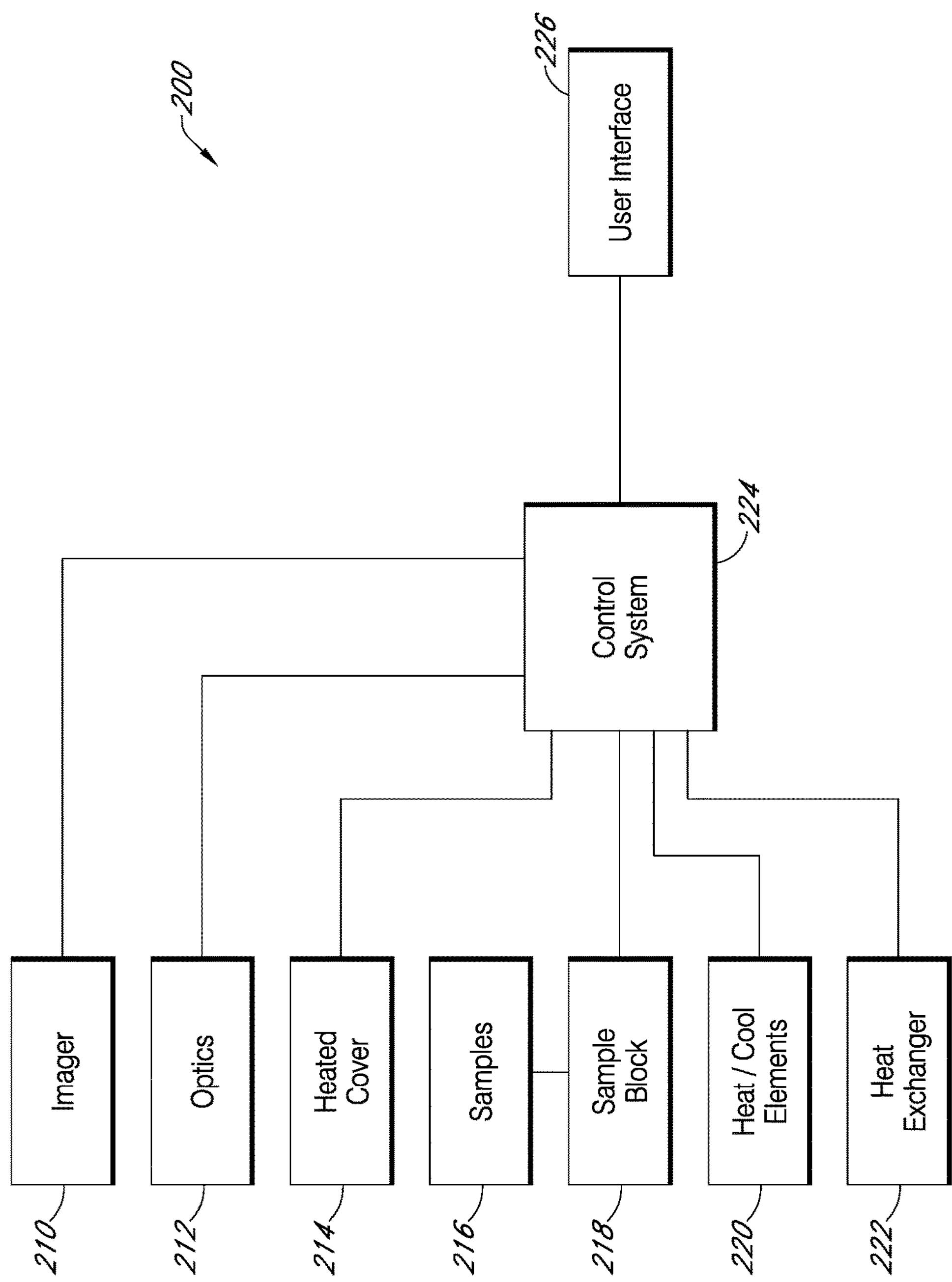
FIG. 2 is a block diagram of an example of some instrument features that may be useful in the processing of protein samples for melt curve analysis.

Various embodiments of methods and systems for the analysis of protein melt curve data according to the present teachings may utilize various embodiments of a cycler instrument as depicted in the block diagram shown in FIG. 2.

As previously mentioned, one way in which proteins may be unfolded is by using thermal unfolding, in which unfolding may proceed as temperature is increased. Various embodiments of systems and methods for the analysis of protein melt curves according to the present teachings may utilize various embodiments of a thermal cycler instrument as depicted in the block diagrams shown in FIG. 2. As shown in FIG. 2, a thermal cycling instrument may include a heated cover 214 that is placed over a plurality of samples 216 contained in a sample support device. In various embodiments, a sample support device may be a glass, metal or plastic slide or substrate with a plurality of sample regions, which sample regions have a cover between the sample regions and heated cover 214. Some examples of a sample support device may include, but are not limited by, a multi-well plate, such as a standard microtiter 96-well, a 384-well plate, a micro device capable of processing thousands of samples per analysis or a microcard, or a substantially planar support, such as various microfluidic devices, microcard devices, and micro chip devices fabricated from, for example, but not limited by, a glass, metal or plastic slide or substrate. The sample regions in various embodiments of a sample support device may include depressions, indentations, holes, ridges, and combinations thereof, patterned in regular or irregular arrays formed on the surface of the slide or substrate. Various embodiments of a thermal cycler instrument may include a sample block 218, elements for heating and cooling 220, and a heat exchanger 222.

Various embodiments of a thermal cycler instrument can process multiple samples simultaneously, and may be used in the generation and acquisition of protein melt curve data. In FIG. 2, various embodiments of a thermal cycling system 200 provide a detection system for the run time acquisition of signals for each sample in a plurality of biological samples, over the entirety the temperature range performed for generating protein melt curve data. A detection system may have an illumination source that emits electromagnetic energy, and a detector or imager 210, for receiving electromagnetic energy from samples 216 in sample support device. Accordingly, though a thermal cycler instrument may be a useful platform for the generation and acquisition of protein melt curve data, one of ordinary skill in the art would recognize that an instrument having detection and sample thermostatting capabilities may be useful for generating protein melt curve data.

A control system 224 may be used to control the functions of the detection, heated cover, and thermal block assembly. The control system may be accessible to an end user through user interface 226 of thermal cycler instrument 200. A computer system 100, as depicted in FIG. 1 may serve as to provide the control the function of a thermal cycler instrument, as well as the user interface function. Additionally, computer system 100 may provide data processing, display and report preparation functions. All such instrument control functions may be dedicated locally to the thermal cycler instrument, or computer system 100 may provide remote control of part or all of the control, analysis, and reporting functions.

As previously described, a large volume of protein melt curve data may be generated as detector signal data collected over the entirety of a defined temperature range for a protein melt assay for each of a large number of samples analyzed during the same run. Given the large volume of data coupled with the complexity of protein melt curve data, various embodiments of systems and methods of the present teachings provide for embodiments of computer readable media that may generate processed data from initial protein melt curve data collected as detector signal output as a function of temperature for each sample in a sample support device.

Additionally, various embodiments of systems and methods of the present teachings provide for embodiments of computer readable media that may allow an end user the flexibility to dynamically analyze large data sets, and selected subsets thereof, using an interactive user interface. Such an interactive user interface may assist an end user in selection of, for example, but not limited by, a new set of analysis parameters, another method by which the data may be analyzed, the review of data for selected replicate sets of data, as well as the associated statistics for the replicate sets, and the review of which sets of data sets may fall within a selected threshold in comparison to a target set of samples.

Figure 3:
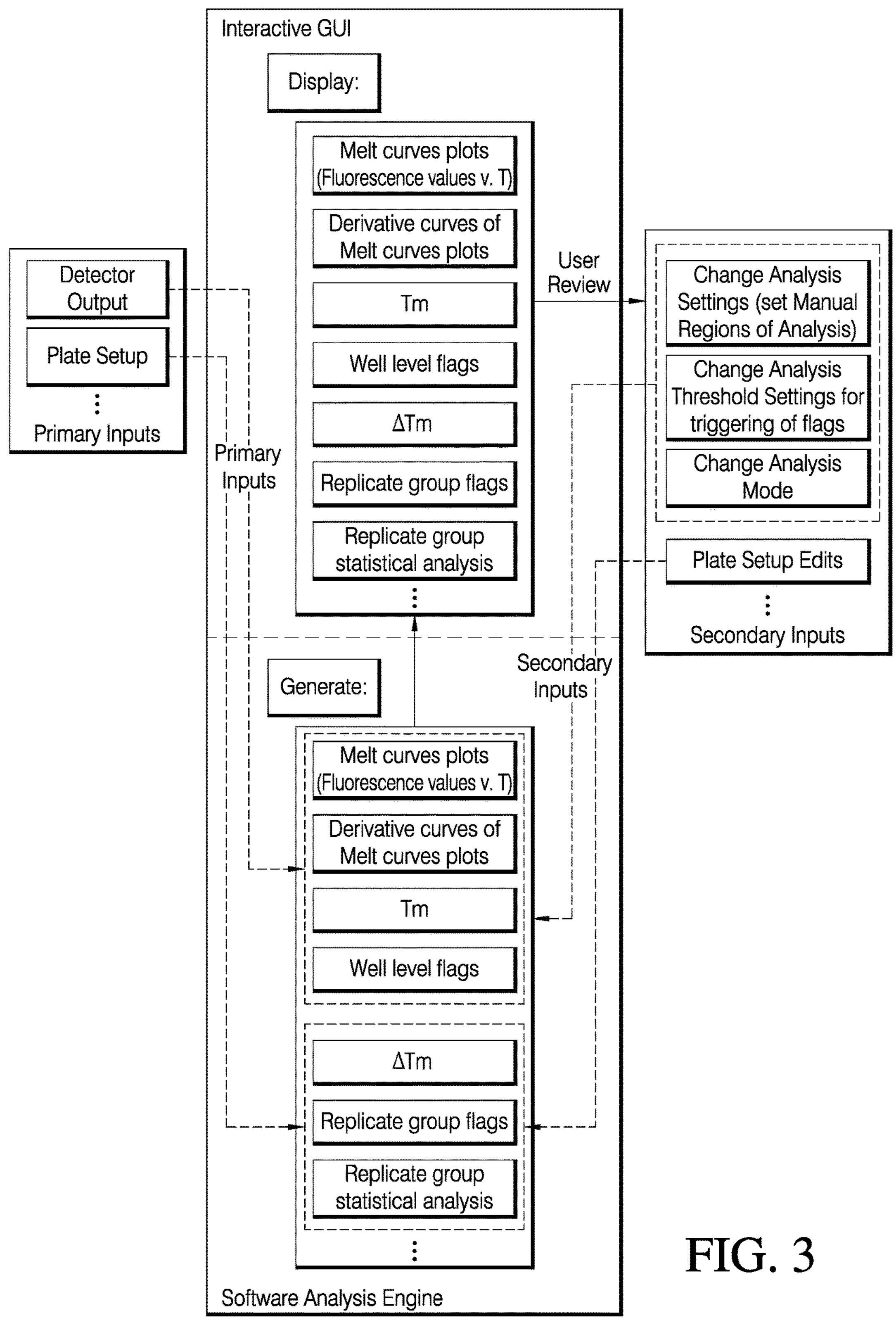
FIG. 3 is representation of an input/output diagram for various embodiments of an interactive GUI for the analysis of melt curve data.

FIG. 3 depicts an input/output diagram meant to convey a process by which various embodiments of systems and methods for the analysis of protein melt curve data may provide an end user the ability to dynamically analyze large data sets of protein melt curve data. As depicted in FIG. 3, primary inputs may include, for example, but not limited by, plate set-up information, as well as the detector output signals collected for each sample over the entire run. Plate setup information includes identifying sample names, and conditions being tested such as buffer, types of ligands or test compounds, type of protein sample, etc. In various embodiments, plate setup information may be later used to identify replicate wells and present final results for each tested condition including replicate statistics. According to various embodiments of systems and methods of the present teachings, plate set-up information may be entered as primary input by an end user before the analysis and then may be imported into the analysis engine in various embodiments of an automated mode of generating results. Such information provides values for conditions, such as, but not limited by sample type, sample concentration, buffer type, as well as numerous other assay conditions. In various embodiments, plate set-up information can be edited manually post-run as secondary input by an end user using manual assignment of values for assay conditions. For various embodiments of systems and methods of the present teachings, an analysis group may be defined by an end user either as primary input before a run and as secondary input during post-run analysis. In various embodiments, an end user may define sample data from an entire sample support device, such as a microtiter plate, as an analysis group. For various embodiments, an analysis group may comprise sample data from a plurality of sample support devices. In various embodiments, an analysis group may be defined by an end user as sample data from selected sample regions, such as wells from a microtiter plate, selected from one or a plurality of sample support devices. In various embodiments, sample data from sample regions selected from a single sample support device may be divided into a plurality of analysis groups. An analysis group may be comprised of data for one sample assayed under the same or different conditions, or may be comprised of a plurality of samples assayed under the same or different conditions, and any combination thereof. Accordingly, various embodiments of systems and methods of the present teachings provide the end user with the dynamic flexibility to define, for example, but not limited by, plate setup information, analysis groups, analysis settings, and threshold settings, Various embodiments of computer readable media, depicted as the analysis engine in FIG. 3, can take primary or secondary input and generate processed melt curve data, for example, but not limited by, melt curve plots of detector signal response versus temperature, nth order derivative plots of the melt curve plots, a determination of a $T_m$, flags for alerting an end user over various aspects of the data and analysis thereof, and replicate group statistics for groups of samples identified by the end user as replicates of a sample, in which various replicate groups may comprise an analysis group. Analysis settings in either an automated or manual mode utilize primary input, such as detector output and plate set-up information, which may be used to generate the well level results for each sample as indicated in FIG. 3. Plate set-up information input by the end user may also be used to compute replicate level results and statistics. In various embodiments of systems and methods for protein melt curve analysis, a user interface may display the results of the processed data from the primary inputs. For various embodiments of systems and methods of the present teachings, once having reviewed the display of the processed data from primary inputs, through a user interface, an end user may change parameters impacting data processing by the selection of secondary inputs. According to various embodiments of systems and methods for protein melt curve analysis of the present teachings, a secondary input is any user input occurring subsequent to the primary input. In that regard, for various embodiments of systems and methods of the present teachings, the number of ways that an end user may iteratively select parameters for analyzing and displaying data is unconstrained. Additionally, an end user may concurrently analyze data from any primary data stored on various types of computer readable media. In that regard, an end user may concurrently analyze data from different instruments, from different runs, from different experimental conditions, or any combinations under which an end user may desire to select and analyze protein melt curve data. Such parameters may include, for example, but not limited by, analysis settings, analysis thresholds, analysis mode, or selection of a method for how a $T_m$ may be determined, methods for comparing a $T_m$ of a sample or replicate group to another sample or replicate group, replicate group display as a function of user-selected experimental variables, and replicate group display as a function of a user-defined threshold. Plate set up related information may particularly impact all results requiring more than one well to generate such as $\Delta Tm$, replicate level flags and statistical analysis.

Figure 4:
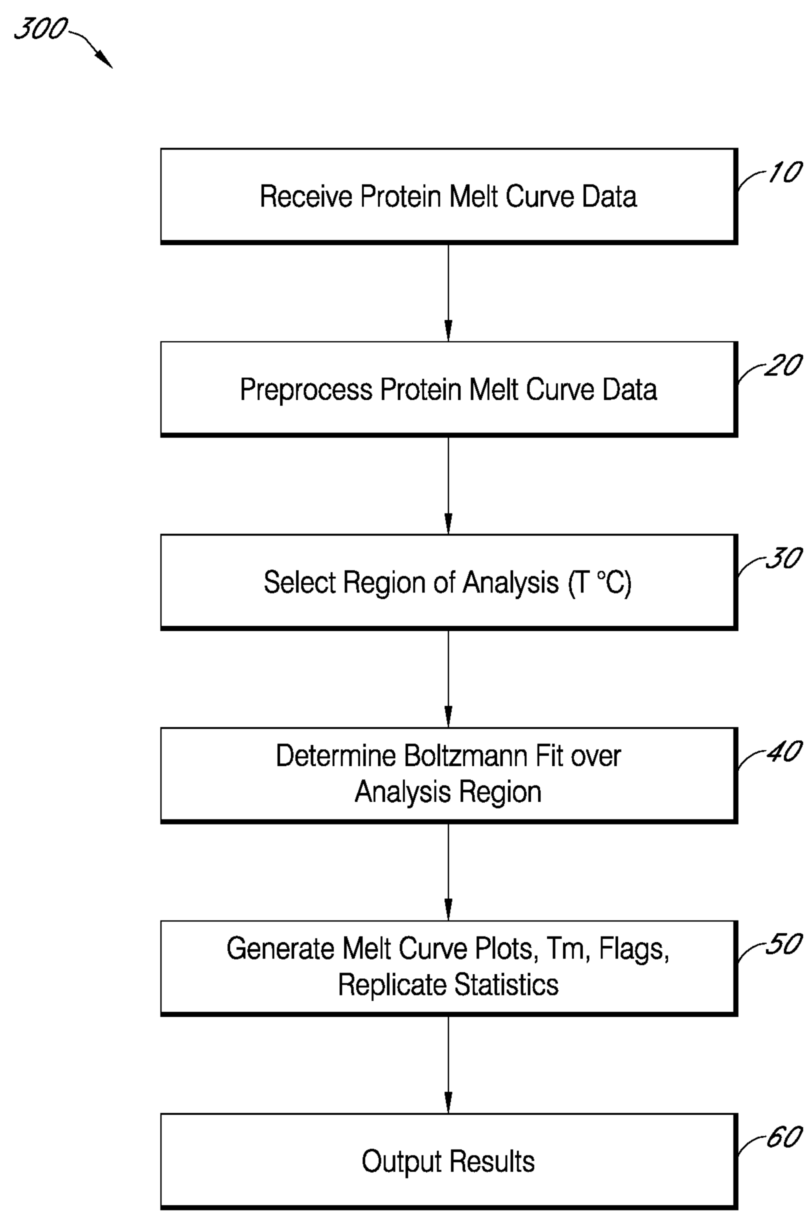
FIG. 4 is a flow chart that depicts various embodiments of systems and methods for the analysis of protein melt curve data.
Figure 5:
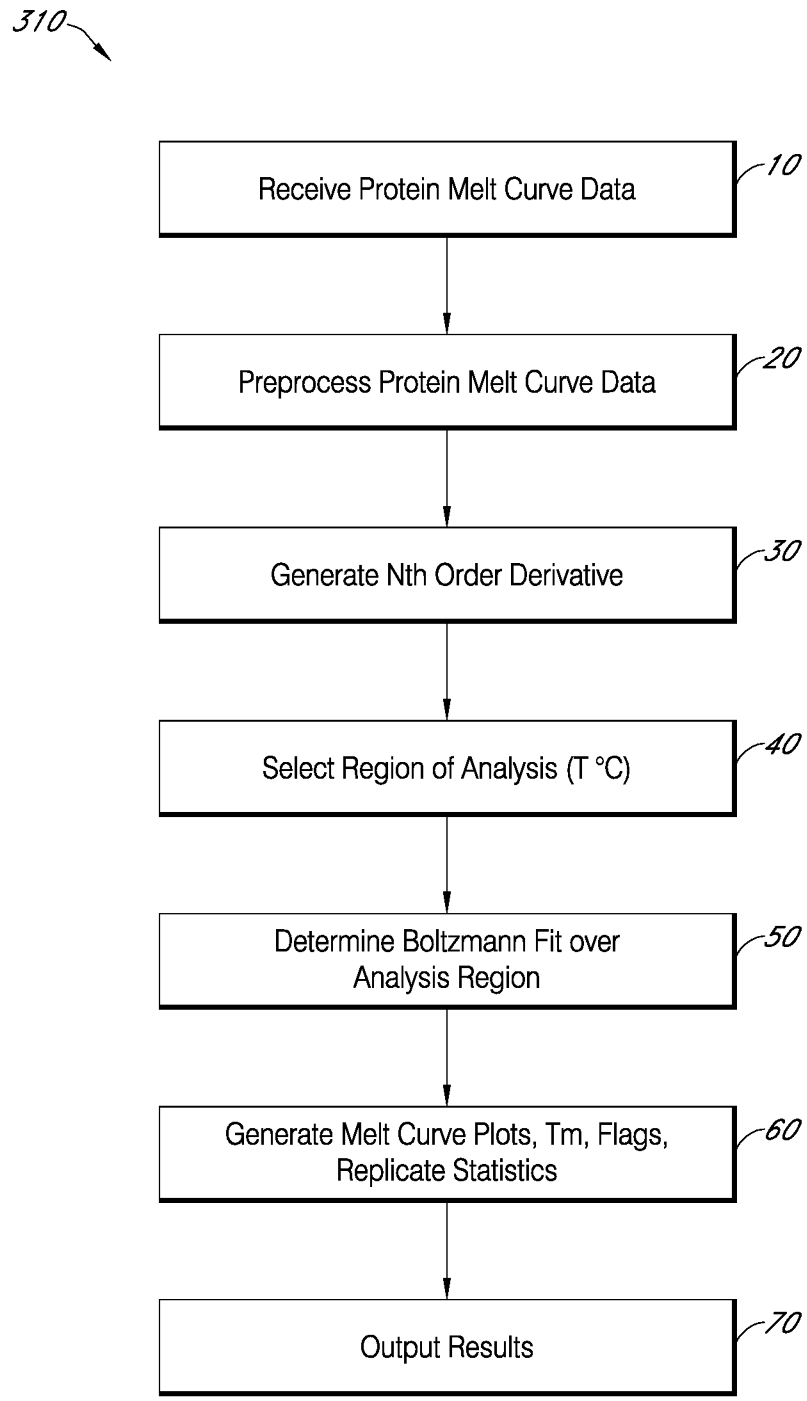
FIG. 5 is a flow chart that depicts various embodiments of systems and methods for the analysis of protein melt curve data.
Figure 6:
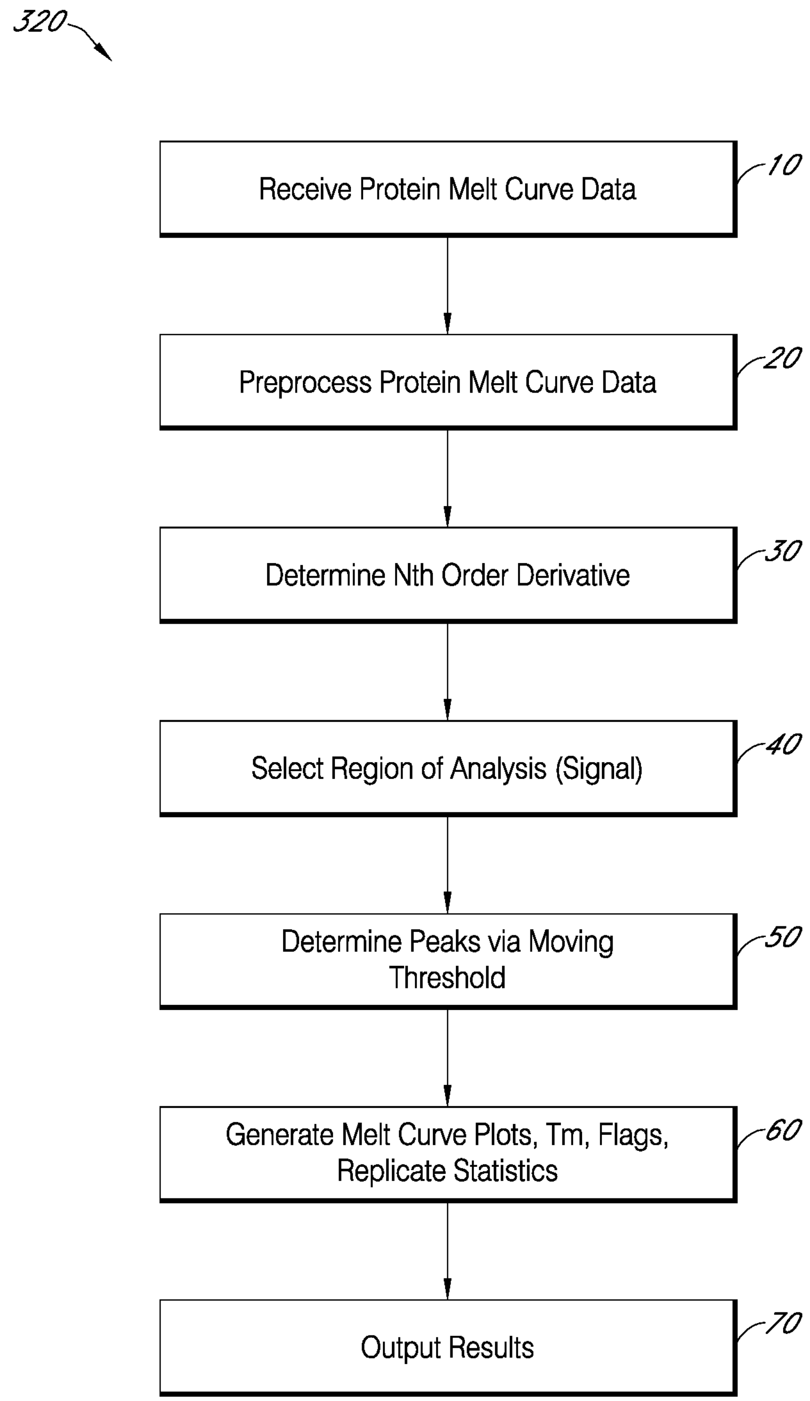
FIG. 6 is a flow chart that depicts various embodiments of systems and methods for the analysis of protein melt curve data.

In FIG. 4-FIG. 6, various embodiments of methods for analyzing initial protein melt curve data are shown. In step 10 of FIG. 3 for method 300, FIG. 4 of method 310, and FIG. 5 of method 320, a data set of initial protein melt curve data is received by a processor for a plurality of samples. As previously described, the initial protein melt curve data comprises a detector signal as a function of temperature for each sample in the plurality of samples In reference to FIG. 4-FIG. 6, step 20 for methods 300 and 310; respectively, preprocessing each of a plurality of sample protein melt curves may be done to denoise the data collected from detection. As one of ordinary skill in the art of signal processing is apprised, denoising data may include process steps such as, but not limited by, cleaning, normalization, transformation, feature extraction, and feature selection. For various embodiments, a first global smoothing step may be done, in which the higher frequency noise components may be removed. In various embodiments, a Fourier transform smoothing may be applied. According to various embodiments, a second local smoothing may be done. In various embodiments, a local regression smoothing may be done, in which a sample melt curve is smoothed sequentially over a defined window. For various embodiments, a window may be selected based on factors such as the number of data points and the system noise. According to various embodiments, a local smoothing function such as, but not limited by, a quadratic regression, a linear regression, and a Savitzky-Golay smoothing function may be applied. In various embodiments, a robust quadratic or linear smoothing function may be used.

With reference to step 30 of FIG. 4 of method 300 and step 40 of FIG. 5 of method 310, for various systems and methods for the analysis of protein melt curve data, after a step of preprocessing data, a step of selecting a region of analysis may be done.

According to various embodiments of systems and methods for the analysis of protein melt curve data, a Boltzmann fit may be applied to a sample protein melt curve, after a step of identifying the region of analysis. According to various embodiments, an equation describing a Boltzmann fit may be given by:

$$F_{Boltzmann}(T) = F_{T_{initial}} + \frac{(F_{T_{final}} - F_{T_{initial}})}{1 + e\wedge(Tm - T/C)} \quad \text{(Eq. 1)}$$

where:

$F_{T_{initial}}$=signal amplitude for an initial temperature over which the data is fit $F_{T_{final}}$=signal amplitude for an final temperature over which the data is fit T=a temperature for any data point between $T_{initial}$ and $T_{final}$ $T_m$=the protein melting temperature for the curve; to be solved for in the fit C=a constant As can be seen by inspection of Eq. 1, the Boltzmann fitting function has a term for a signal amplitude at an initial temperature and a signal amplitude at a final temperature. According to various embodiments, as indicated in step 30 of FIG. 4 for method 300 and step 40 of FIG. 5 for method 310, a region of analysis defining an initial and a final temperature range for fitting the data may be identified. According to various embodiments as indicated in step 30 of FIG. 5 for method 310 and FIG. 6 for method 320, at least one nth order derivative of the data may be done on a sample protein melt curve for selecting a region of analysis. In various embodiments, a first derivative of the data may be taken. For various embodiments, a first derivative of the smoothed data may be taken, and the derivative signal may be further smoothed to remove high frequency components. Accordingly, for various embodiments, regions of monotonic rise of signal may be identified from regions of positive signal value on this smoothed derivative profile. In various embodiments, the longest and steepest segment of signal rise may be selected as the region of analysis. In various embodiments, a first derivative of the data may be taken. For various embodiments, a first derivative of the smoothed data may be taken. According to various embodiments, higher order derivatives may be taken of the initial or smoothed data. In various embodiments, the derivative signal may undergo various scaling (such as inversion) to improve the mathematical and/or data presentation properties of the signal to identify the region of analysis accurately.

As depicted in step 40 of FIG. 4 for method 300 and 50 of FIG. 5 for method 310, a best-fit melting temperature $T_m$ for a sample curve may be found. According to various embodiments, and in reference to equation 1, a best-fit $T_m$ may be derived from the Boltzmann fitting function, when a best fit has been determined. According to various embodiments, the constant, C, is solved for in the fitting process against sample protein melt curve data through a self-consistent process, in which the constant is defined in an iterative process of fitting the data to equation 1. For various embodiments, a best-fit may be converged upon in the fitting process when a mean-squared error term converges on a threshold value. According to various embodiments, an algorithm such as the Levenberg-Marquardt algorithm may be used to search various parameters of a model for which a minimum error between data, such as protein melt curve data, and a nonlinear least squares fit to such data will be reached.

For various embodiments of method 300, as shown in FIG. 4, method 310 of FIG. 5, and method 320 of FIG. 6, a Boltzmann equation, as shown in Eq. 1, may provide a fit to a variety of protein melt curve data, having variability over a plurality of analytical attributes. For various embodiments, analytical attributes may include, for example, but not limited by curve shape, background signal, change in signal amplitude, and noise.

According to various embodiments of method 310 of FIG. 5 and 320 of FIG. 6, in addition to an nth order derivative providing the basis for identifying a region of analysis, a $T_m$ value may be determined by using an nth order derivative. According to various systems and methods of the present teachings, an end user may use a $T_m$ value determined by using an nth order derivative to compare to a $T_m$ value determined by Boltzmann fit. In various embodiments, an end user may select either the Boltzmann determined $T_m$ value or the $T_m$ value determined by an nth order derivative.

For various embodiments of method 320 of FIG. 6, a moving threshold may be used on nth order derivative data to identify peaks. For various embodiments of method 320 of FIG. 6, steps 10-30 may be performed as described previously for the corresponding steps of method 300 of FIG. 4 and method 310 if FIG. 5. As one of ordinary skill in the art is apprised, proteins may undergo multiphasic melting. Accordingly, for such proteins, there may be a plurality of $T_m$ values that may be determined for a melt curve of a protein undergoing multiphasic melting. An end user may analyze a multiphasic melt curve using a Boltzmann fit to various selected regions of analysis, according to various embodiments of method 300 of FIG. 4 and method 310 of FIG. 5. Additionally, an end user may analyze a multiphasic melt curve according to various embodiments of method 320 of FIG. 6.

For various embodiments of method 320 of FIG. 6, at step 40, a region of analysis may be selected within signal limits $R_1$ and $R_2$ of an nth derivative plot of a multiphasic melt curve. In various embodiments, limits $R_1$ and $R_2$ of an nth derivative plot of a multiphasic melt curve may be between about 20% to about 99% of the signal value. For various embodiments, limits $R_1$ and $R_2$ of an nth derivative plot of a multiphasic melt curve may be between about 10% to about 99% of the signal value. For various embodiments, the lower limit may be selected so that it is clearly at or above an analytical signal distinguished from background noise. In various embodiments, an end user may select the limits $R_1$ and $R_2$ of an nth derivative plot of a multiphasic melt curve.

According to various embodiments of method 320 of FIG. 6, at step 50, a threshold value may be sequentially moved in a stepwise fashion within the limits $R_1$ and $R_2$ of an nth derivative plot of a multiphasic melt curve. According to various embodiments, the number of threshold values taken in a stepwise fashion may be between about 50 threshold values to about 1000 threshold values. In various embodiments, the number of threshold values taken in a stepwise fashion may be between about 200 threshold values to about 600 threshold values. For various embodiments, the number of threshold values taken in a stepwise fashion may be selected by an end user. For example, there may be features in an nth derivative plot of a multiphasic melt curve, such as shoulder peaks, and noise, which vary from assay to assay, and instrument to instrument. For an nth derivative plot of a multiphasic melt curve having small shoulder features, a greater number of steps may be necessary in order to analyze such features. In contrast, for noisy data, too many steps may result in analyzing artifacts. Additionally, increasing the number of the number of threshold values taken in a stepwise fashion between signal limits $R_1$ and $R_2$ increases the analysis time.

Figure 7:
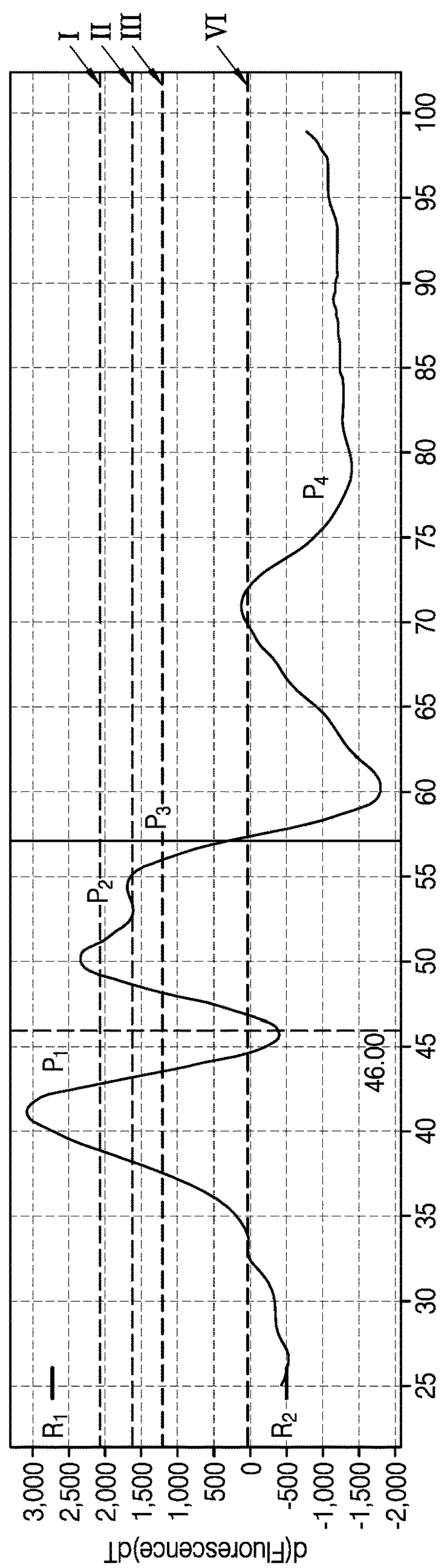
FIG. 7 is a graphical representation illustrating various embodiments of methods for peak selection for multiphase protein melting.

According to various embodiments of method 320 of FIG. 6, at step 50, a peak may be identified as a contiguous region that falls above a threshold at any one threshold value at any one step. In various embodiments, for a contiguous region in which more than one peak may be visually apparent in data inspected by an end user, the peak of greatest magnitude may be counted as the peak at that step. For example, in FIG. 7, a first derivative graph of a multiphasic melt for a protein is depicted. In FIG. 7, each of lines I-VI represents a threshold value that was selected in four different steps. At each of a sequential threshold I-II, a peak may be defined as a contiguous region above the threshold. For example, in FIG. 7, at threshold I of step 1, 2 peaks ($P_1$ and $P_2$) would be determined, while at threshold II of step 2, 3 peaks ($P_1$, $P_2$, and $P_3$) would be determined. However at threshold III of step 3, a contiguous region including $P_2$ and $P_3$ occurs, so that only $P_2$, the peak of greatest magnitude, is counted. Then, for threshold III of step 3, 2 peaks ($P_1$ and $P_3$) are counted. Finally, in threshold VI of step 6, three peaks ($P_1$, $P_2$, and $P_4$) are counted.

For various embodiments of method 320 of FIG. 6, a threshold may be sequentially moved in a stepwise fashion between limits $R_1$ and $R_2$ of an nth derivative plot of a multiphasic melt curve, and the frequency of counted peaks determined. According to various embodiments, a normalization value may be obtained based on the highest frequency of counts for a peak, as:

$$\text{Norm}=\max(N_1,N_2, \ldots N_n)$$

In this expression, $N_1$, $N_2$, . . . $N_n$ represent the number of times peaks ($P_1$, $P_2$ . . . $P_n$) are counted in a stepwise count for a sequentially moving threshold value between limits $R_1$ and $R_2$ of an nth derivative plot of a multiphasic melt curve. Additionally, for various embodiments of method 120 of FIG. 3, a peak detection frequency value may be determined for each peak as:

$$\Gamma(n)=N_1/\max(N_1,N_2, \ldots N_n),N_2/\max(N_1,N_2, \ldots N_n), \ldots N_n/\max(N_1,N_2, \ldots N_n)$$

In this expression, the peak detection frequency for each peak is determined as a quotient of the number of times a peak is counted in a stepwise count for a sequentially moving threshold divided by the normalization value.

According to various embodiments of method 320 of FIG. 6, a rejection limit, may be set on Γ(n), so that any peak having a value less than a selected limit is not counted:

$$X\ \%=N_r/\max(N_1,N_2, \ldots N_n)$$

Figure 8:
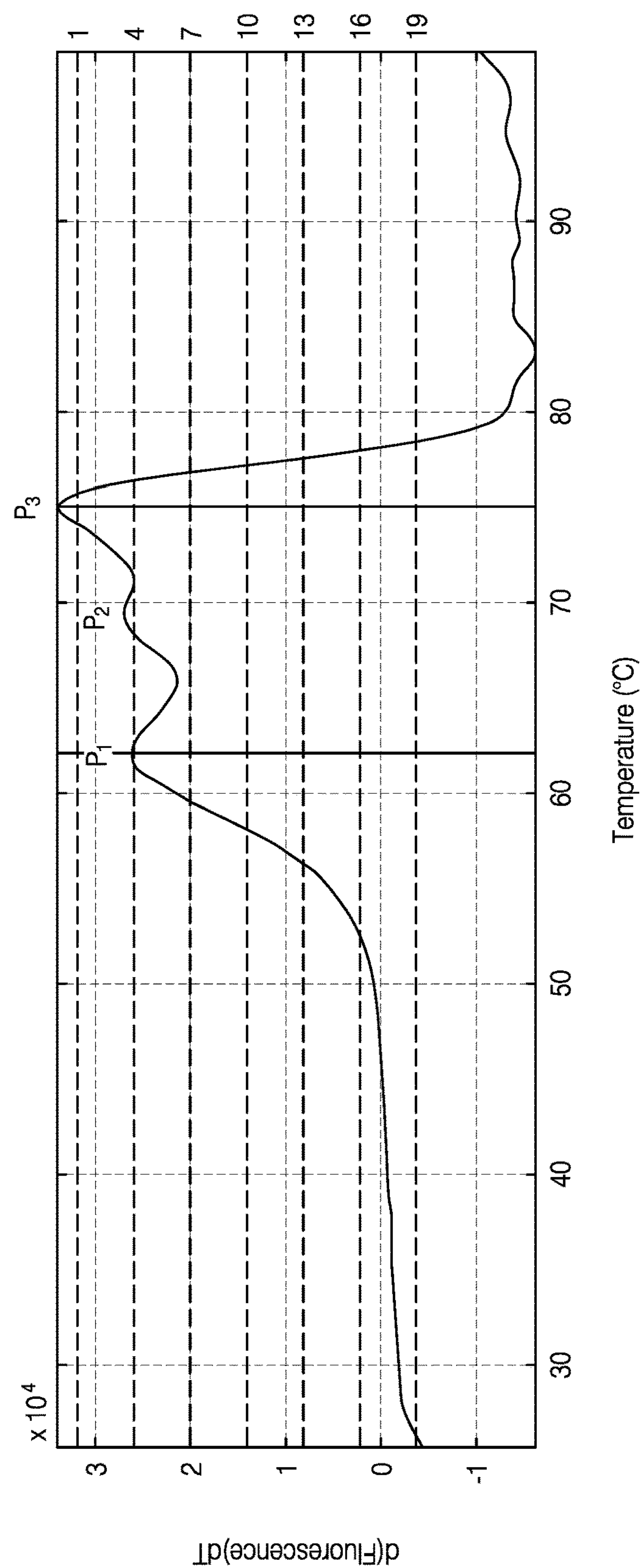
FIG. 8 is a graphical representation illustrating various embodiments of methods for peak selection for multiphase protein melting.

In various embodiments the rejection limit, X %, may be between about 0.5% to about 6%. In various embodiments, an end user may select a rejection limit. An example of various embodiments of method 120 of FIG. 3 is depicted in FIG. 8. In FIG. 8, 19 sequential stepwise threshold values were taken, and the number of peaks was determined at each of the 19 threshold values. In this example, $P_1$ is counted 3 times with a Γ(1) of 16%, $P_2$, is counted 1 time with a Γ(1) of 5% and $P_3$ is counted 19 times for a Γ(1) of 100%. For a rejection limit set at 2%, all peaks in this example would be selected as peaks having a $T_m$ value determined by the first derivative peak value. For a rejection limit set at 6%, $P_2$ would be rejected, and 2 peaks, $P_1$ and $P_3$, would be selected as peaks having a $T_m$ value determined by the first derivative peak value.

In various embodiments of systems and methods for the analysis of protein melt curve data according to the present teachings, and with respect to step 50 of FIG. 4 of method 300, and step 6 of; FIG. 5 and FIG. 6 for methods 310 and 320, respectively, the analysis engine, as depicted in FIG. 3, may generate processed data. As previously discussed, the analysis engine may generate processed data from both primary and secondary inputs, in which a secondary input is any user input occurring subsequent to the primary input. In that regard, for various embodiments of systems and methods of the present teachings, an end user may iteratively select parameters for analyzing and displaying data. Such parameters may include, for example, but not limited by, analysis settings, analysis thresholds, methods for how a $T_m$ may be determined, methods for comparing a $T_m$ of a sample or replicate group to another sample or replicate group, replicate group display as a function of user-selected experimental variables, and replicate group display as a function of a user-defined threshold, and plate set-up information entered by an end user as a secondary input. In this fashion, an end user may interactively and iteratively analyze data and subsets of data generated from both within and between run analyses for potentially large sets of protein melt curve data. In that regard, an end user may concurrently analyze data from any primary data stored on various types of computer readable media. Accordingly, an end user may concurrently analyze data from different instruments, from different runs, from different experimental conditions, or any combinations under which an end user may desire to select and analyze protein melt curve data. Results thus generated may be displayed graphically and additionally presented in tabular format. According to various embodiments, as will be discussed in more detail subsequently, such graphical and tabular displays may be synchronized dynamically on the same display. Accordingly, selecting row entries on in a tabular format will highlight corresponding plots on the graphical display area. In various embodiments, an end user r may independently zoom in on any graphic for detailed review of information. For various embodiments, information displayed in a tabular format may be sorted by, for example, using a mouse or key stroke to select any of a plurality of attributes entered as column header names, thereby providing for the information in the tabular format to be sorted by a selected attribute.

Figure 9:
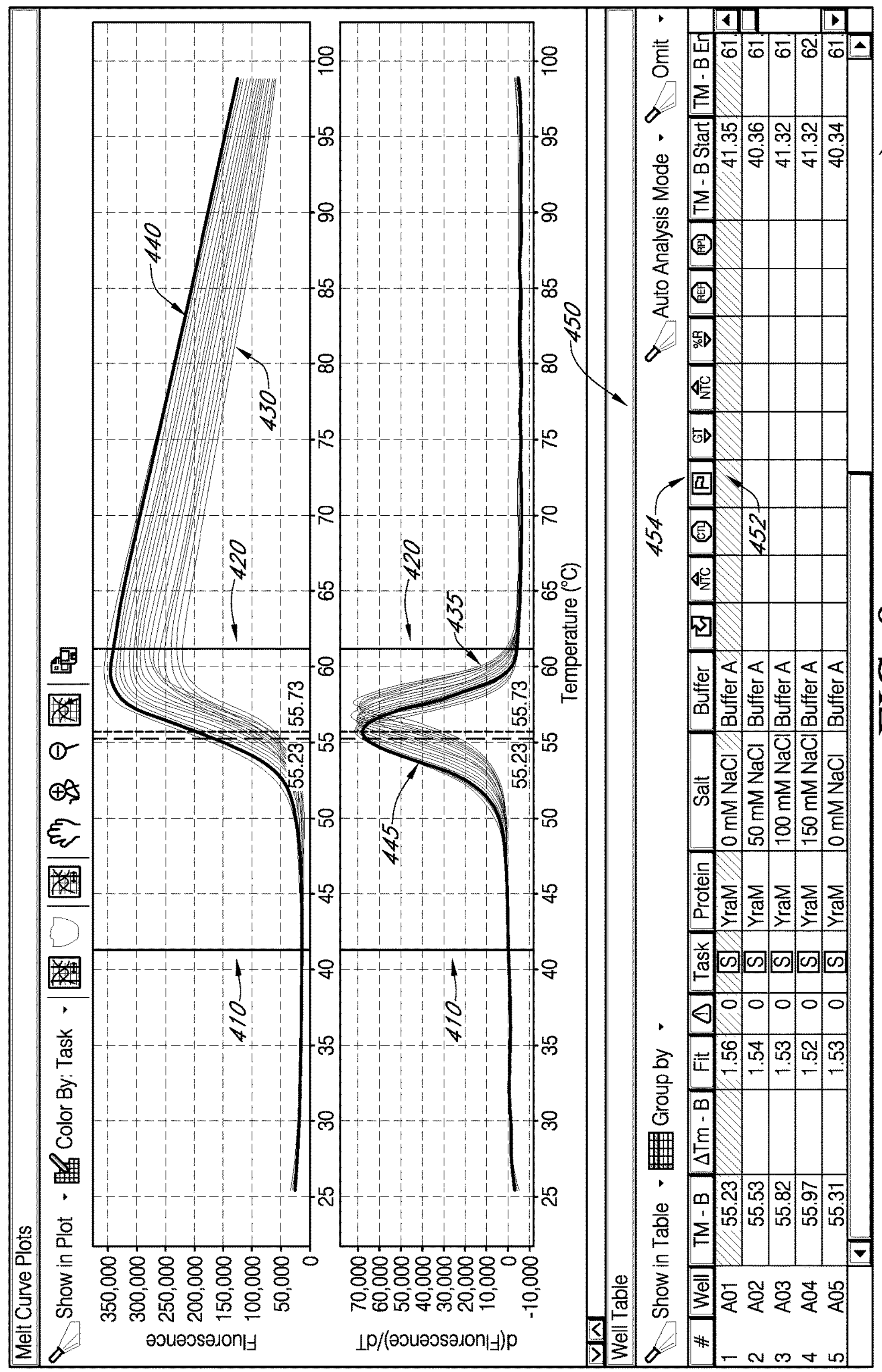
FIG. 9 is an exemplary window of an interactive GUI according to various embodiments of systems and methods according to the present teachings.

For example, as can be seen by inspection of Eq. 1, the Boltzmann fitting function has a term for a signal amplitude at an initial temperature and a signal amplitude at a final temperature. According to various embodiments, as shown in FIG. 9, an interactive GUI 400 may provide a display of a region of analysis defining an initial 410 and a final 420 temperature range for a Boltzmann fit to the data 430 in comparison to an nth order derivative of the data 435. In various embodiments, a first derivative of the data may be taken, as shown in FIG. 9. For various embodiments of an interactive GUI displaying a Boltzmann fit to the data 430 in comparison to a first derivative of the data 435, the data may be dynamically synchronized to a data table listing of the samples 450. For various embodiments, a sample line 452 may be highlighted in the table by an end user, which allows the corresponding data 440, 445 to be visually apparent in the Boltzmann fit data set 430, and first derivative set of data 435, respectively. In various embodiments, an end user may select any line or combination of lines for selective viewing of the corresponding graphs. Additionally shown on sample table 450 is an example of a flag icon, 454, which may alert an end user to a number of factors impacting data quality and data analysis, as will be discussed in more detail subsequently. The dynamic synchronization of data table listing of samples 450 with data plots 430, 435, may facilitate an end user to visually evaluate selected groups of data, and may allow for rapid iteration of such evaluation. For example, but not limited by, such dynamic synchronization may allow an end user to evaluate whether or not a Boltzmann fit is an appropriate fit for selected groups of data. Moreover, flags alerting an end user to factors impacting data quality and data analysis may facilitate end-user review of critical issues impacting the overall quality of analysis.

Figure 10A:
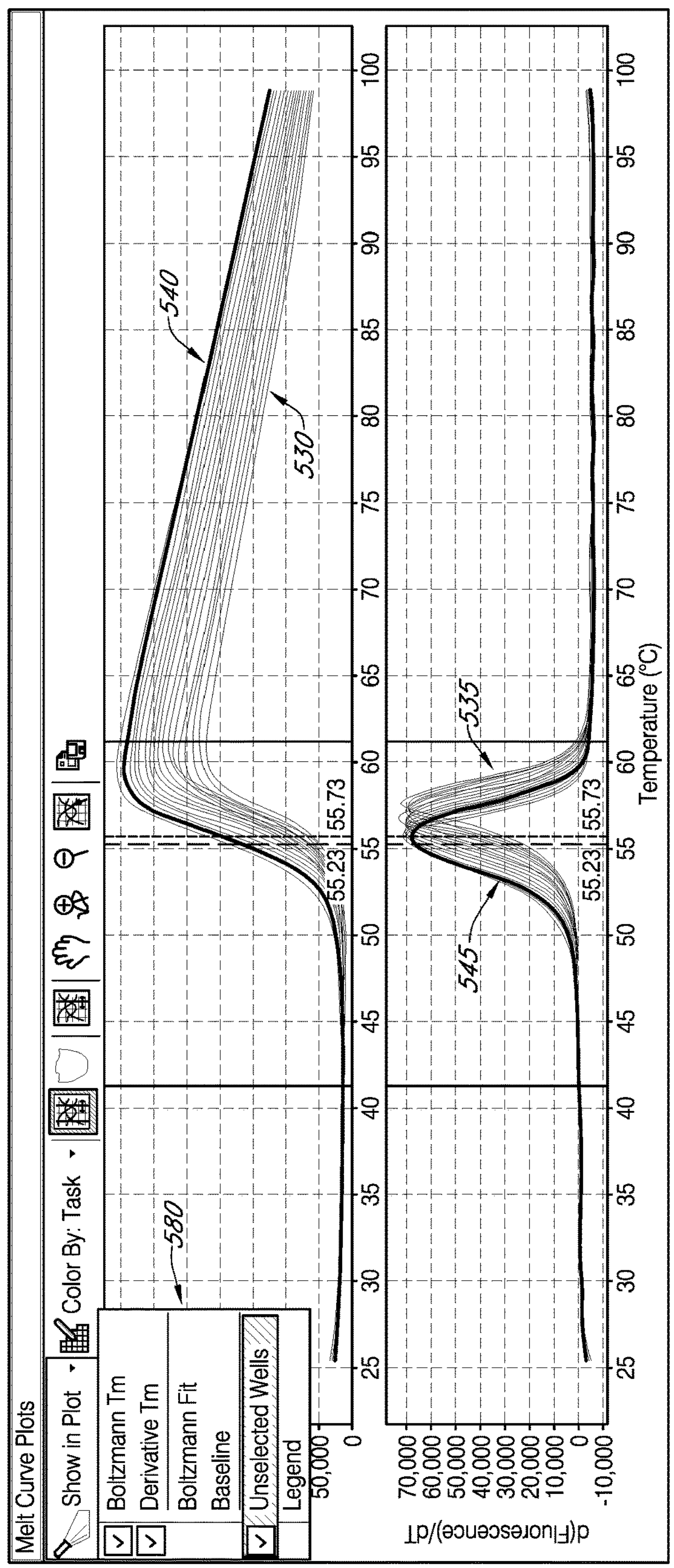
FIG. 10A and FIG. 10B are exemplary portions of a embodiments of GUI of FIG. 9, which displays the effect of a selection of a function from an exemplary popup window.
Figure 10B:
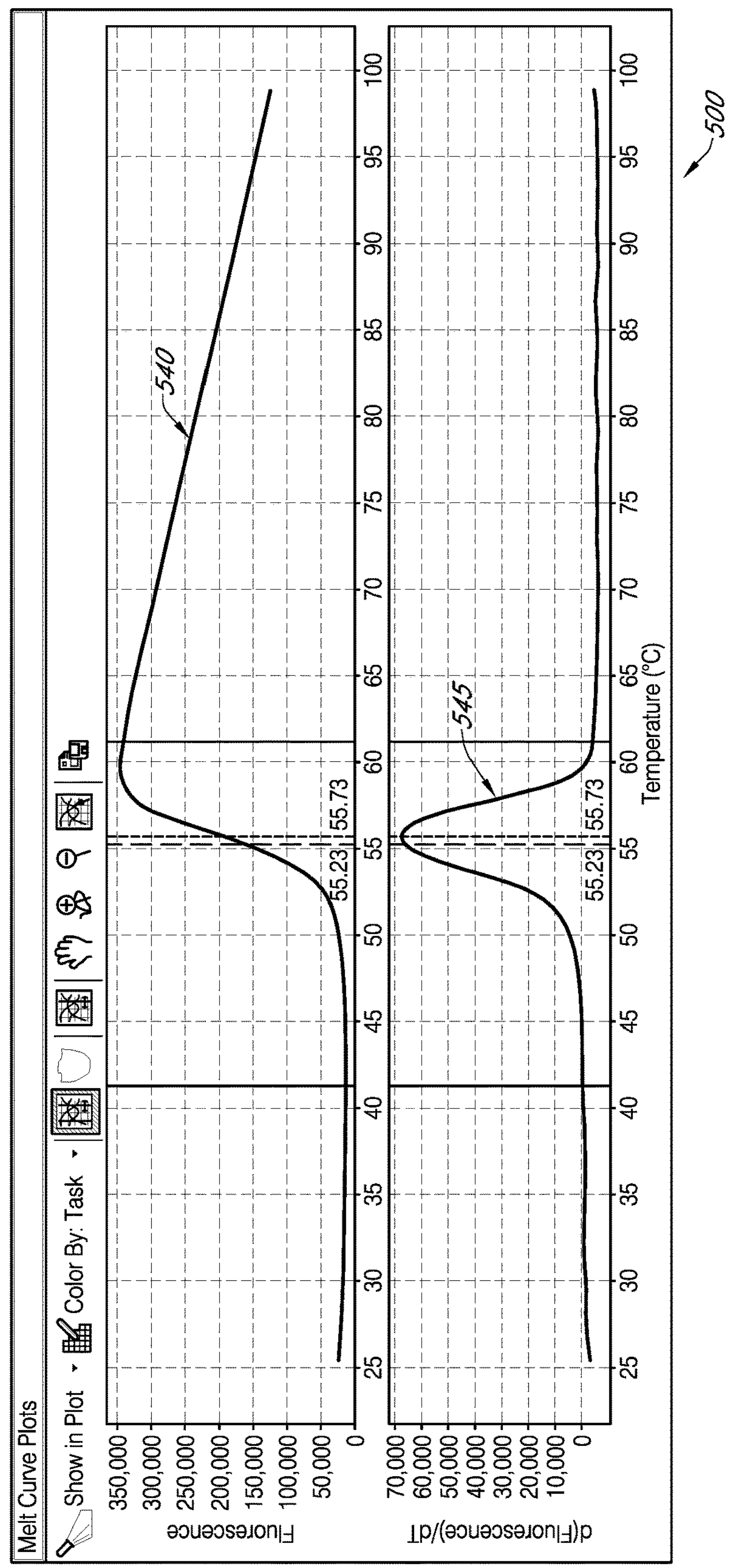

While in FIG. 9 a graph dynamically selected by an end user is highlighted in a Boltzmann fit graph 440 and a first derivative graph 445, allowing comparison to the full data sets, in various embodiments of an interactive GUI according to the present teachings, as shown in FIG. 10A and FIG. 10B, an interactive GUI 500, may allow an end user may make a selection from a popup window 580 (FIG. 10A) that allows for viewing only the selected Boltzmann fit data 540 and the corresponding first derivative data 545 (FIG. 10B). In addition to well level data review within the context of all the data analyzed, an end user may want to assess the data within the context of the various experimental conditions. To this end, an assay condition studied may be input by an end user as associated with a color.

Figure 11:
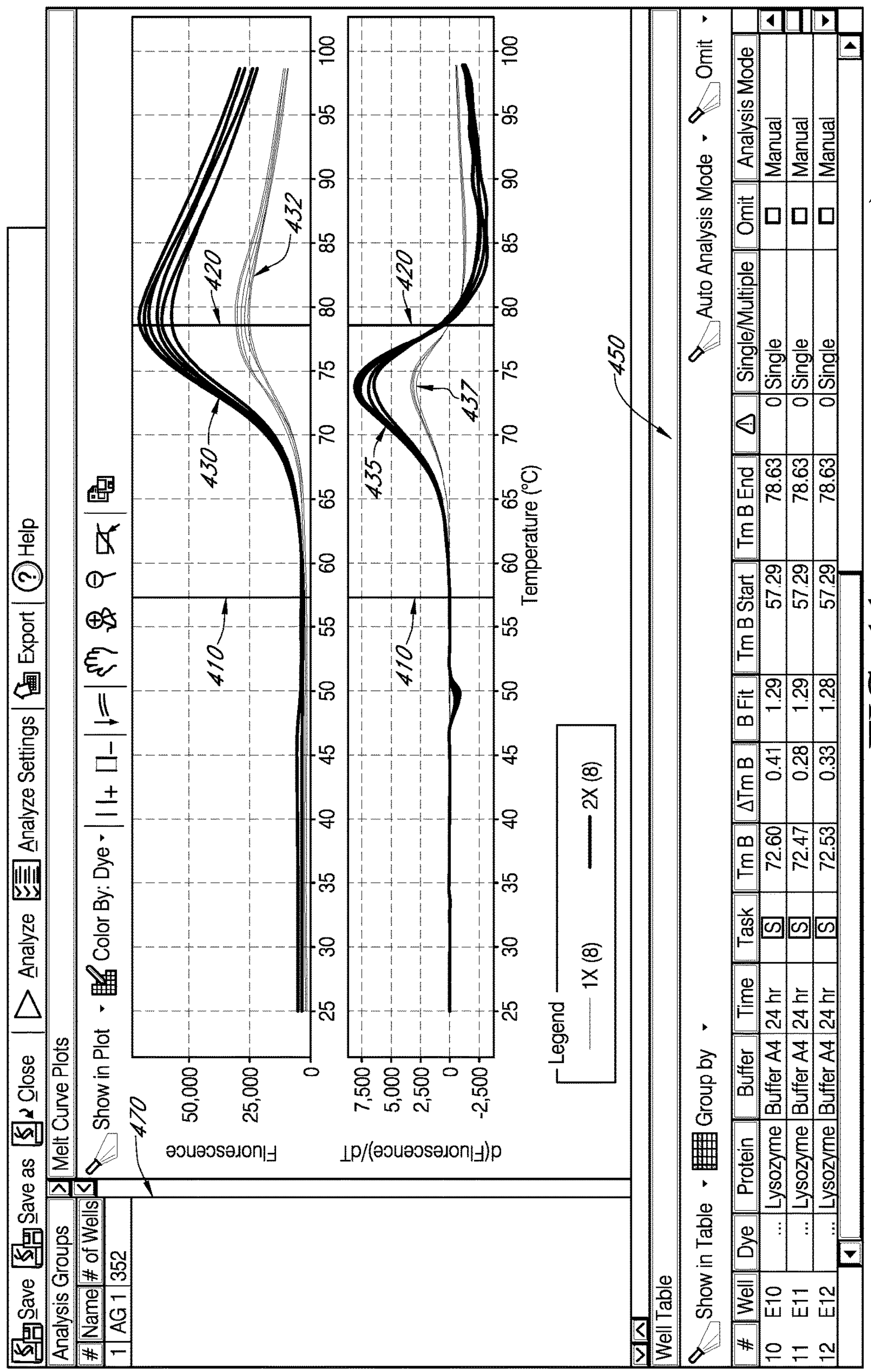
FIG. 11 is an exemplary window of an interactive GUI according to various embodiments of systems and methods according to the present teachings.

These color associations may be retained by the analysis engine and can be invoked in the graphical display as shown in FIG. 11 where the curves are colored coded by the attribute value of a specific condition. The data used in the display shown in FIG. 11 were generate as a time-course study in which dye concentrations were varied, so the variables displayed use of color coding to indicate time and dye concentration. According to various embodiments, a different condition category may be selected by an end user from, for example, a drop down menu. "According to various embodiments, an end user may use color to further enhance data analysis while maintaining the synchronized interactivity between the tabular and graphical formats. As previously discussed with respect to FIG. 3, if an end user edits plate set-up details during data review; such secondary input will be taken into consideration and the use of color for displaying attributes will be re-displayed with the new color coding for the well level attribute values.

As depicted in FIG. 11, the region of analysis is bounded by a first temperature selection 410 and a second temperature selection 420, which may be automatically determined or manually selected by an end user. In FIG. 11, the two sets of curves, 430 and 432 are taken from a same time point in the study, but indicate differences in dye concentrations. As depicted in FIG. 11, Curves 435 and 437 are first derivative plots of curves 430 and 432 respectively. Sample table 450 indicates information for sample data selected from a single sample support device in a plurality of sample support devices that were used to define an analysis group for the data presented in part in FIG. 11.

As previously mentioned, analysis groups may be selected in a variety of ways by an end user. Recalling, an end user may define sample data from an entire sample support device, such as a microtiter plate, as an analysis group. For various embodiments, an analysis group may comprise sample data from a plurality of sample support devices. In various embodiments, an analysis group may be defined by an end user as sample data from selected sample regions, such as wells from a microtiter plate, selected from one or a plurality of sample support devices. In various embodiments, sample data from sample regions selected from a single sample support device may be divided into a plurality of analysis groups. An analysis group may be comprised of data for one sample assayed under the same or different conditions, or may be comprised of a plurality of samples assayed under the same or different conditions, and any combination thereof. Further, an analysis group may be defined by an end user either as primary input before a run and as secondary input during post-run analysis. Though for the purpose of illustration, two sets of sample data are displayed from this study in FIG. 11; window 470 indicates that the sample data included for display is taken from an analysis group defined by 352 sample regions, in this example, sample wells, taken from a plurality of sample support devices, in this example, microtiter plates. In various embodiments, sample data defining an analysis group may be selected from between about 1 to about 100 sample support devices. As such, various embodiments of systems and methods according to the present teachings provide an end user with the capability of interactively displaying and dynamically analyzing a large and complex amount of data.

As previously discussed, protein melt data may be affected by a variety of analytical attributes, such as, but not limited by curve shape, background signal, change in signal amplitude, and noise. Additionally, proteins as a class of biopolymers may have complex melt curves, given the complexity of primary and secondary structure on tertiary and quaternary folding motifs. In that regard, providing an end user flexibility to evaluate complex protein melt curve data for a plurality of samples in a sequential and rapid manner through an interactive GUI may facilitate the data analysis process.

Figure 12:
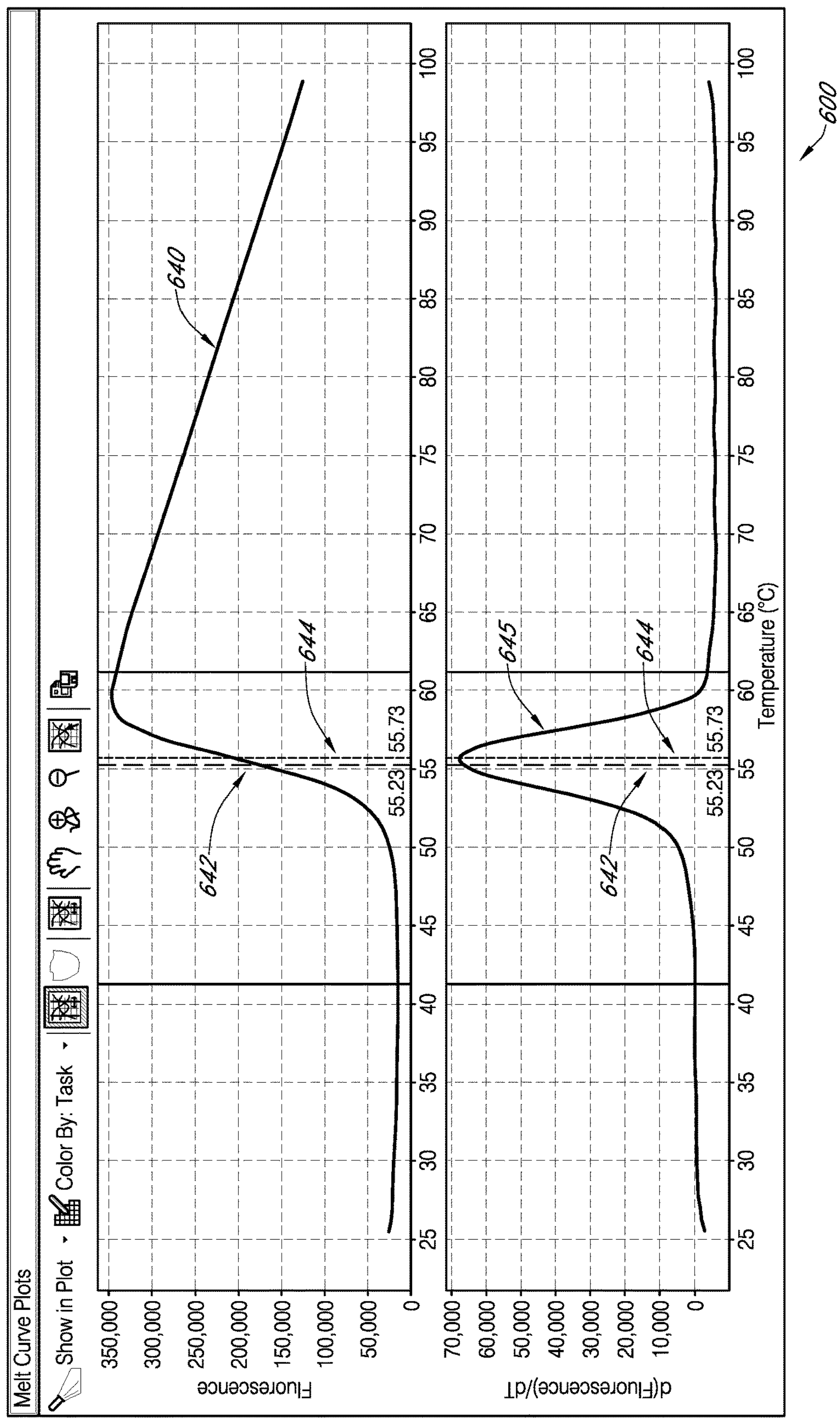
FIG. 12 is an exemplary portion of embodiments of an interactive GUI of FIG. 9, which displays the interactive nature for an end user comparing various embodiments of a determination of a melt temperature ($T_m$).

According to various embodiments of an interactive GUI according to the present teachings, interactive selections by an end user may be made, which enable the rapid and sequential evaluation of a data for a plurality of samples in a protein melt curve experiment. For example as shown in GUI 600 of FIG. 12, for curve 640, the evaluation of a $T_m$ 642 determined for a Boltzmann fit of curve 640 versus a $T_m$ 644 determined by an nth derivative 645, may provide an end user with a tool for evaluation of whether or not a Boltzmann fit is appropriate for the data being evaluated. As can be seen for this example, the $T_m$ 642 determined for a Boltzmann fit 640 versus a $T_m$ 644 determined by a first order derivative 645 is fairly close. However, as will be discussed subsequently, given the complexity of protein melt data, the comparison may provide an end user with tools for deciding how a $T_m$ may be determined.

As previously mentioned, the determination of a $T_m$ for protein melt curve data may be done from a Boltzmann fitted data, after a step of identifying the region of analysis. For various embodiments of an interactive GUI 700 of FIG. 13 according to the present teachings, an end user may readily and iteratively change the region of analysis for a Boltzmann graph and synchronously for an nth order derivative graph, such as first derivative graph. This can be done by, for example, but not limited by a drag and draw interactive tool. Such an interactive tool would allow an end user to select a new analysis region of analysis by moving initial first bound 710 to a new first bound 711. Additionally, an end user to select a new analysis region of analysis by moving initial second bound 720 to a new second bound 721. For various embodiments of systems and methods according to the present teachings, as shown in FIG. 3, an analysis engine may then generate and display data according to the new input from an end user. An iterative selection of a region of analysis may give an end user a rapid, visual means for understanding the impact of the selection of a region of analysis on the determination of a $T_m$ for protein melt curve data.

Though the comparison of a $T_m$ determined using a Boltzmann fit may be evaluated by inspecting it in relationship to the determination of a $T_m$ determined using an nth order derivative, such as a first derivative, various embodiments of an interactive GUI according to the present teachings may also provide additional tools for such an evaluation. According to various embodiments of an interactive GUI 800 of FIG. 14, a Boltzmann fit 810 may be visually displayed coincident to a data curve 840, and synchronously to an nth order derivative curve, such as first derivative curve 845. As previously discussed for FIG. 12, a $T_m$ 842 determined from the Boltzmann fitted data 810 may be directly compared to a $T_m$ 844 determined from an nth order derivative curve 845.

Figure 14:
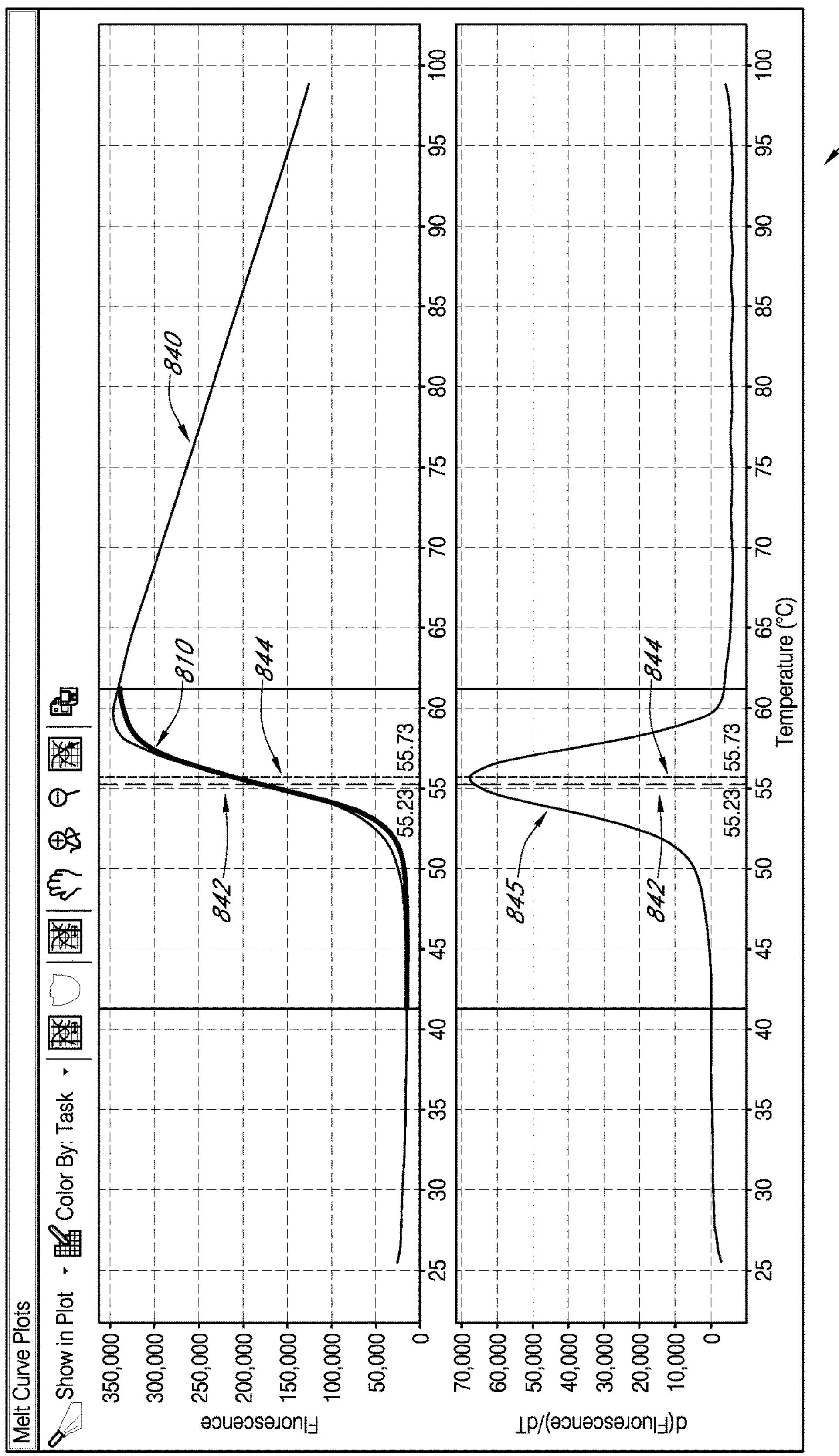
FIG. 14 is an exemplary portion of embodiments of an interactive GUI of FIG. 9, which displays the facility for viewing a fit of the data for selected data for various embodiments a determination of a melt temperature ($T_m$).
Figure 15:
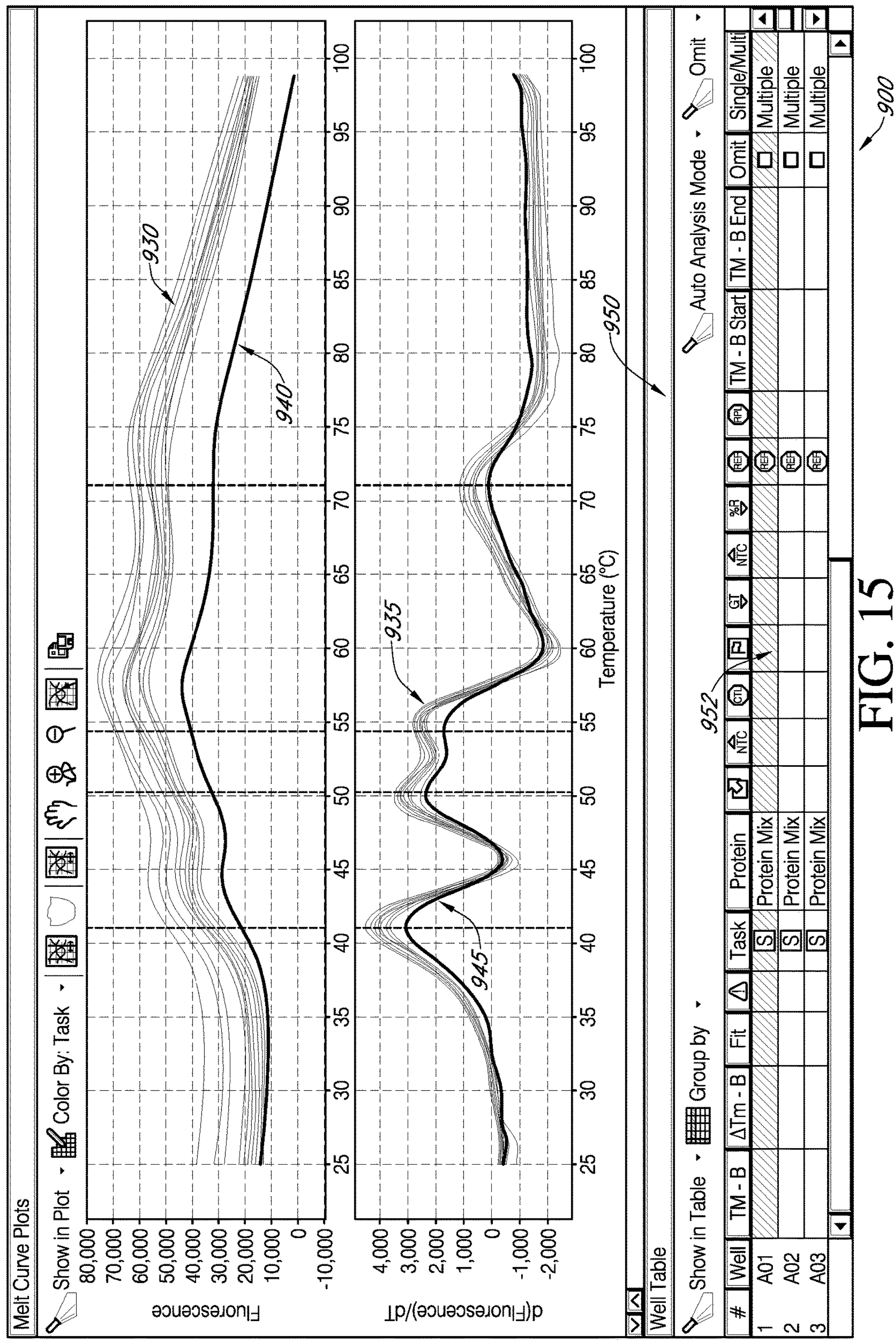
FIG. 15 is an exemplary portion of embodiments of an interactive GUI of the present teachings, which displays the facility for viewing a fit of the data exhibiting multiphase melting.

The complex nature of protein structure lends itself to multi-phase melt curves, for which there may be a $T_m$ determined for each phase transition. Such a set of multi-phase data is depicted in FIG. 14 and FIG. 15. For such multi-phase melt curve data a Boltzmann fit may not be an appropriate fit model. In various embodiments of an interactive GUI 900 of FIG. 15, an end user may select a subset of data 952 from a sample table 950, which subset of data 952 for a multi-phase set of sample melt curves 930 become visually apparent 940, and synchronously apparent 945 for a nth order derivative set of curves 935. In this fashion, an end user may sequentially select any of a set of data from sample table 952, and view the data in the melt curve set 930, as well as in the nth order derivative set of curves 935. Such an interaction GUI display may allow an end user to readily determine a $T_m$ for each of a phase transition of a protein displaying a multiphasic melt profile.

Figure 16:
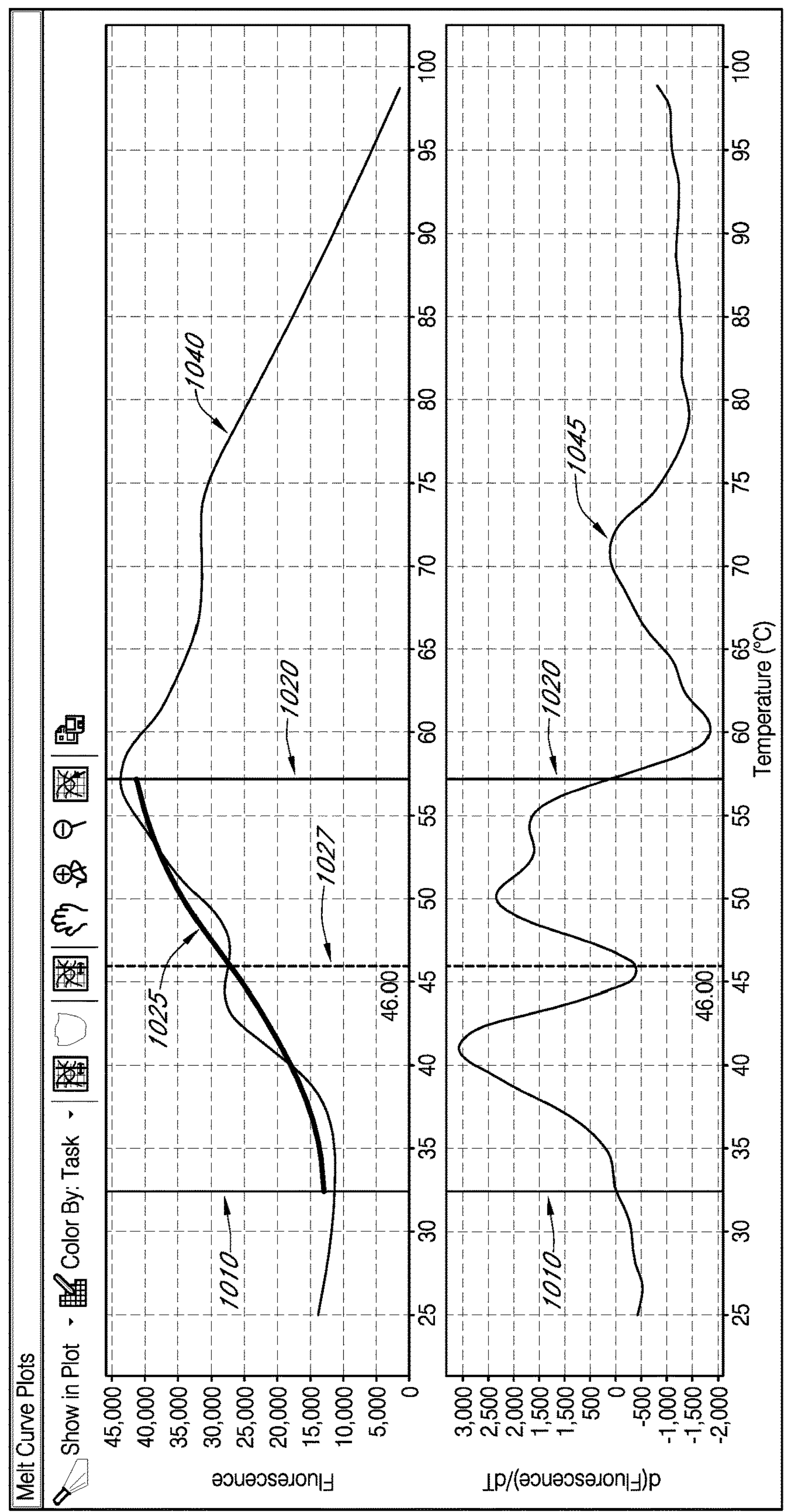
FIG. 16 is an exemplary portion of embodiments of an interactive GUI of FIG. 14, which displays the facility for viewing a fit of the data exhibiting multiphase.

Alternatively, as shown in an interactive GUI 1000 of FIG. 16, an end user can specifically chose to display just the subset of data selected in the sample table. According to various embodiments of an interactive GUI according to the present teachings, an end user may evaluate a Boltzmann fit 1025 to a melt curve 1040 over a defined analysis region having a first bound 1010 and a second bound 1020, and having a $T_m$ 1027 determined for that selected fit. For various embodiments of GUI 1000, a derivative curve 1045 may be synchronously displayed. As can be seen by inspection of FIG. 16, such a $T_m$ determination may be significantly different for a Boltzmann fit selected as the mode or method of analysis than for each phase separately determined.

As previously mentioned, various embodiments of systems and methods of the present teachings may use the color in a graphical display to provide an end user with a tool for visually identifying, for example, but not limited by, various experimental conditions. As such, discrete values of an attribute or condition studied may be color coded by input from an end user in plate set-up information. As shown in FIG. 16, color may also be utilized to distinguish between fitted curve 1025 versus mutliphasic curve 1040. Accordingly, various embodiments of systems and methods of the present teachings may utilize various format selections for graphic display of sample data, such as color or line type, to provide an end user with ease of readily visually differentiating various graphic entries of sample data according to a plurality of variables.

Figure 13:
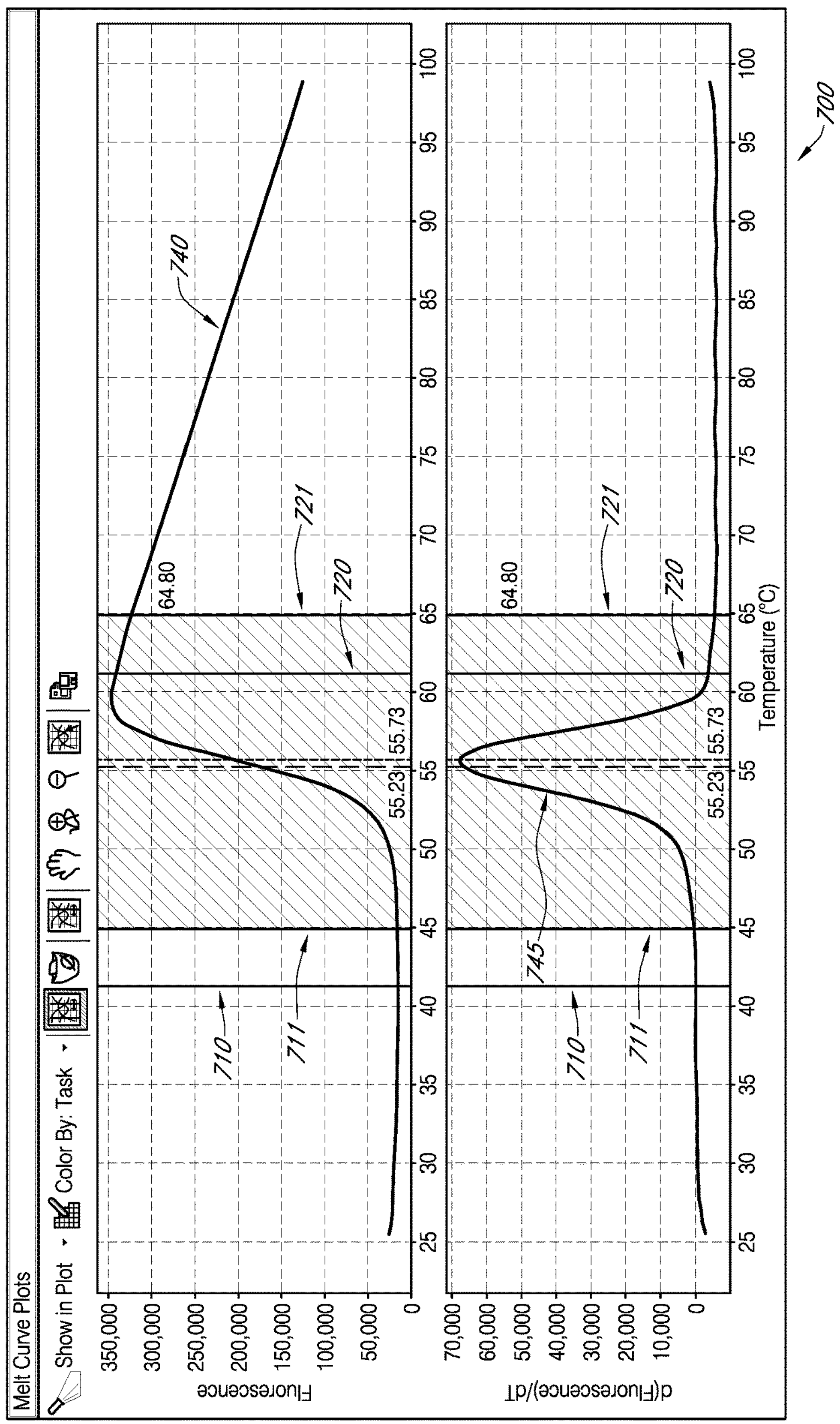
FIG. 13 is an exemplary portion of embodiments of an interactive GUI of FIG. 9, which displays the interactive nature for an end user selecting a target temperature region for analysis for various embodiments a determination of a melt temperature ($T_m$).

Additionally, for either GUI 900 of FIG. 15 or GUI 1000 of FIG. 16, as previously discussed for FIG. 13, an end user may utilize an interactive means for selecting an analysis region for each of the phases in a multi-phase melt data.

Figure 17B:
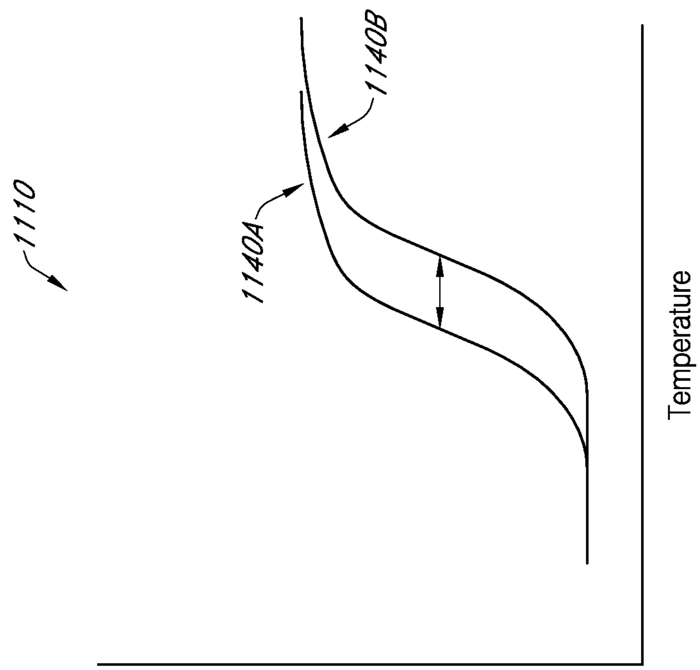
FIG. 17A and FIG. 17B display a feature of an interactive GUI according to various embodiments for a system providing protein melt analysis, which displays the facility for viewing a plurality of curves by aligning curves to a common y-axis.
Figure 17A:
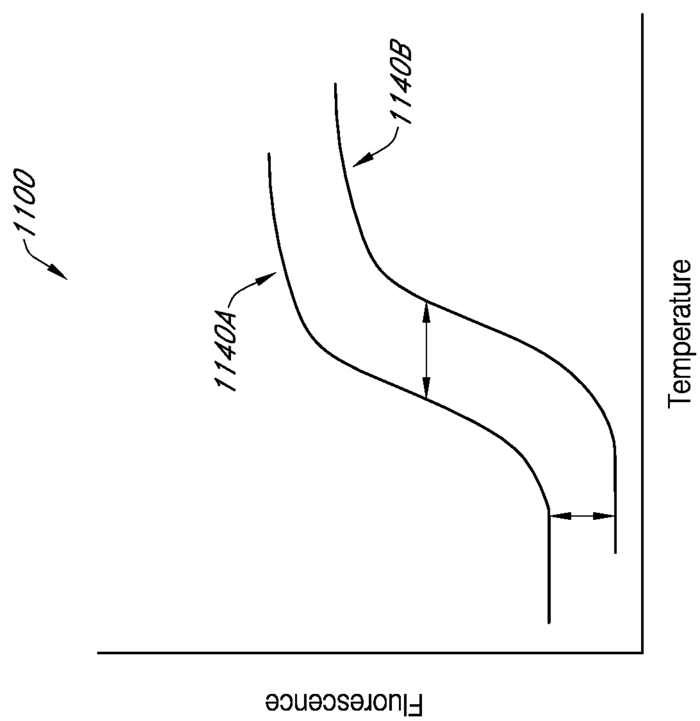

As shown, for example, but not limited by, in FIG. 9 in comparison to FIG. 15, it appears that the baselines for the plurality of melt curves 430 of FIG. 9 are substantially aligned, while it appears that the baselines for the plurality of melt curves 930 in FIG. 15 appear to be shifted over a range of ordinate values. According to various embodiments of the present teachings, an end user may ready align the curves. As depicted in interactive GUI 1100 and 1110 of FIGS. 17A and 17B, respectively, an end user may select an alignment function from a popup box (not shown) for aligning curves 1140A and 1140B, as shown in FIG. 17A, resulting in the alignment as depicted in FIG. 17B. In various embodiments, once the alignment function is selected by an end user, a mean ordinate offset is calculated, and the curves in a selected set of curves are then adjusted to the mean value, so that they are aligned as shown in FIG. 17B. Such a baseline alignment feature may, for example, allow an end user to visually compare similarities and differences between curves in a selected set of curves. For example, but not limited by, such a baseline alignment feature may allow an end user to evaluate an x-offset, or may allow for the evaluation of the difference in curve shapes in a selected data set.

Various embodiments of an interactive GUI according to the present teachings may facilitate an understanding of the impact of experimental variables on a plurality of samples in a protein melt data set. Such variables may include, for example, but not limited by, neutral salt type and concentration, chaotropic agent type and concentration, buffer type; pH and concentration, protein sample, and analysis group. For various embodiments of systems and methods for the analysis of protein melt curve data, an analysis engine, as depicted in FIG. 3, may determine various replicate group statistics for a selected analysis group. Such replicate group statistics may include, for example, but not limited by, expressions of central tendency, such as mean, and median values, as well as expression of variance, such as standard deviation, and CV %. As depicted in FIG. 3, such replicate group statistics one determined from primary or secondary input may then be displayed on an interactive user interface.

Figure 18:
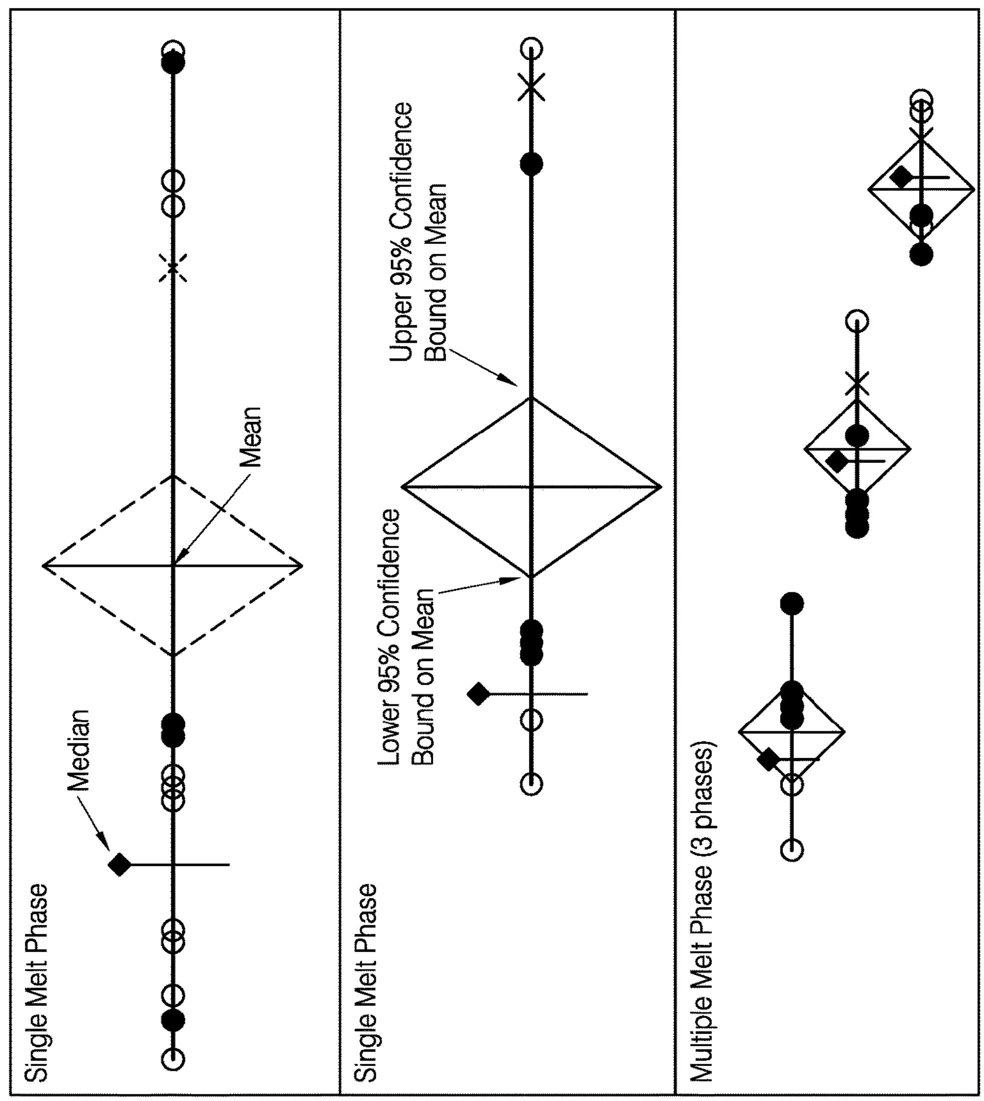
FIG. 18 is display feature of an interactive GUI according to various embodiments of the present teachings for conveying information concerning replicate data groups.

For example, various embodiments of an interactive interface according to the present teachings may be displayed as depicted in frames I-III of FIG. 18. In the top two frames of FIG. 17, plot (I) is a visual depiction of replicate group statistics for a set of reference replicate samples. For replicated group statistics generated by an analysis engine on a user-selected set of replicate data, replicate group statistics may be visually represented.

According to various embodiments of an interactive GUI according to the present teachings, as depicted in FIG. 18, replicate group statistics may be visually represented in part by a diamond plot, as shown in plot (I). For this diamond plot, the mean of $T_m$ values is indicated by a first vertical line intersecting a first set of apices, while a second set of apices intersected by the horizontal line represent 95% confidence intervals of the mean. The median of $T_m$ values generated by the analysis engine on the user selected set of replicate data is depicted as a second, and distinct vertical line. For this example, the replicate group statistics for plot (I) was generated by user-selected data for a set of reference samples run on two separate sample support devices for separate analyses run using various embodiments of computer and instrument systems as previously described. The replicate $T_m$ values for each sample from each plate may be readily visually identified as a first set depicted by white circles and a second set depicted by black circles. Such as visual display of central tendency and variance for $T_m$ values may readily allow an end user to evaluate, for example, data quality. For example, the data point represented by an "X" is a data point that was selected by an end user to be omitted, based on an analysis flag, as will be discussed in more detail subsequently. Additionally, visual comparison of replicate group statistics $T_m$ values may allow for a ready understanding of experimental results. In that regard, as the representation shown in plot II of FIG. 18 is for an experimental set of samples selected for comparison to the reference set of samples in plot I. As shown, at a glance, an end user may readily compare the replicate group statistics of the reference and experimental set. For example, but not limited by, an end user may readily discern at a glance the average $T_m$ for the experimental set of samples has been shifted to a higher temperature than that of the average $T_m$ for reference set of samples. Additionally, the shape of the diamond plot is visually about the same, indicating the variance of the two data sets is approximately the same. According to various embodiments of systems and methods of the present teachings, a variety of geometric and line shapes, colors, and formats may be used to visually impart to an end user replicate group protein melt curve data.

In FIG. 18, plot III shows a staggered set of replicate group statistics for a data set having a triphasic melt. As will be discussed in more detail subsequently, for such multiphasic protein melt transitions, an average $T_m$ may be determined for each transition, and the associated visually variance reflected in a user interface.

As previous discussed in the example of flag 454 of FIG. 9, various embodiments of systems and methods for the analysis of protein melt curve data provide for alerting an end user, for example, but not limited by, about initial data attributes, such as quality of signal, detection of multiple phases, as well as analysis issues, such as problems with curve fitting and replicate group comparisons. In FIG. 19, a table showing some types of issues for which an end user may be altered is shown. As can be seen in FIG. 19, for each type of issue that may be identified for various embodiments of systems and methods for protein melt curve analysis, an icon may be selected. The association of an icon with a flag may then act as a ready visual alert of the entire number of samples run, or any subset thereof. Subsets of these flags are well-level (sample-level) flags that are not altered by plate set-up edits, which may be input by an end user as secondary input, according to FIG. 3. The remaining replicate group flags are altered by plate set up edits, which may alter the designation of samples comprising a replicate group.

Figure 20:
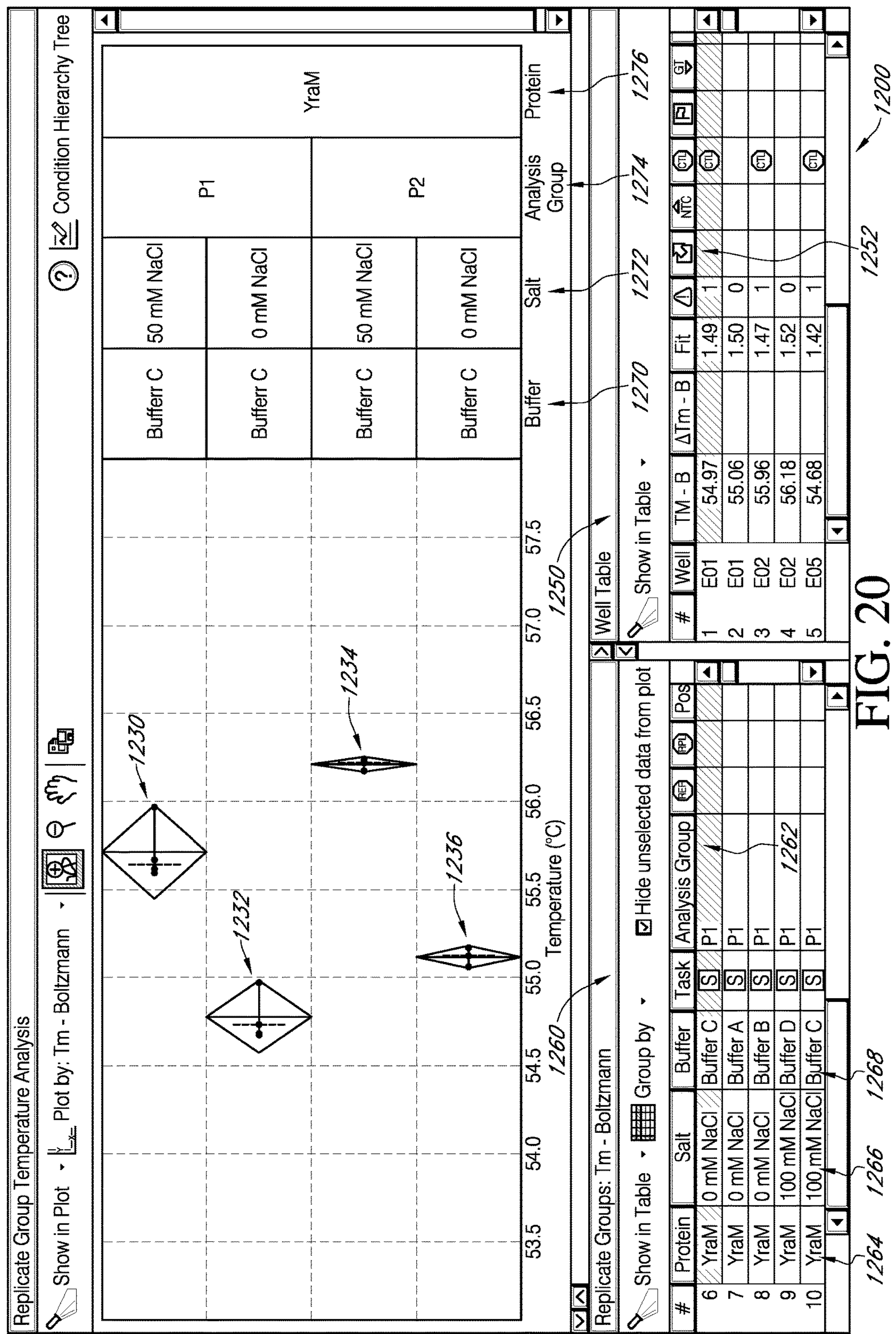
FIG. 20 depicts an exemplary portion of a feature of an interactive GUI according to various embodiments for a system providing protein melt analysis, which displays the facility for viewing the effect of various parameters on replicate data groups.

For various embodiments of an interactive GUI 1200 of FIG. 20, a replicate group table 1260 may be provided to an end user in addition to a sample well table 1250, as previously discussed. Replicate group table 1260 may include a selection of replicate samples belonging to an identified group 1262 of a sample protein 1264, as well as various experimental variables (1266, 1268). According to various embodiments of systems and methods of the present teachings, replicate group data (1230-1236) may be viewed, for example, with respect to $T_m$ values for a selected set of experimental variables 1270-1276, which in GUI 1200 are displayed as buffer, salt, analysis group, and protein, respectively. The replicates may be represented by diamond plots 1230-1236, which as was previously discussed, visually convey important information about replicate group central tendency and variance. Non-overlapping diamond plots visually display the impact that experimental variables may have on, for example as shown in FIG. 13, the $T_m$ values for a selected set of replicates. As shown in interactive GUI 1200 of FIG. 9, experimental variables are shown both in the replicate group table 1260, as well as next to the display of the replicate group data (1230-1236).

Figure 21:
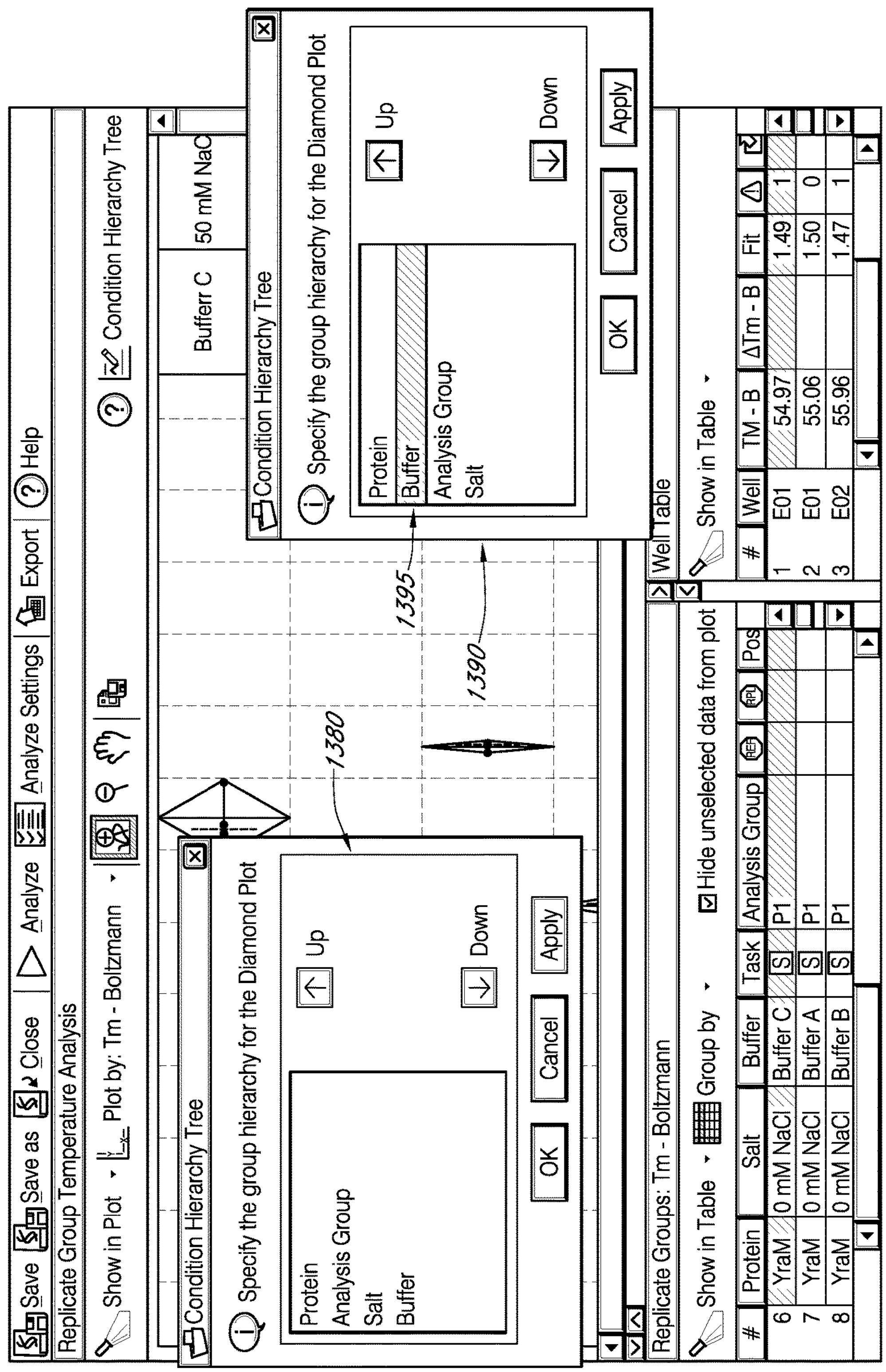
FIG. 21 depicts an exemplary portion of a feature of an interactive GUI according to various embodiments for a system providing protein melt analysis, which displays the facility for viewing the effect of various parameters on replicate data groups via a selection from an exemplary popup window.
Figure 22:
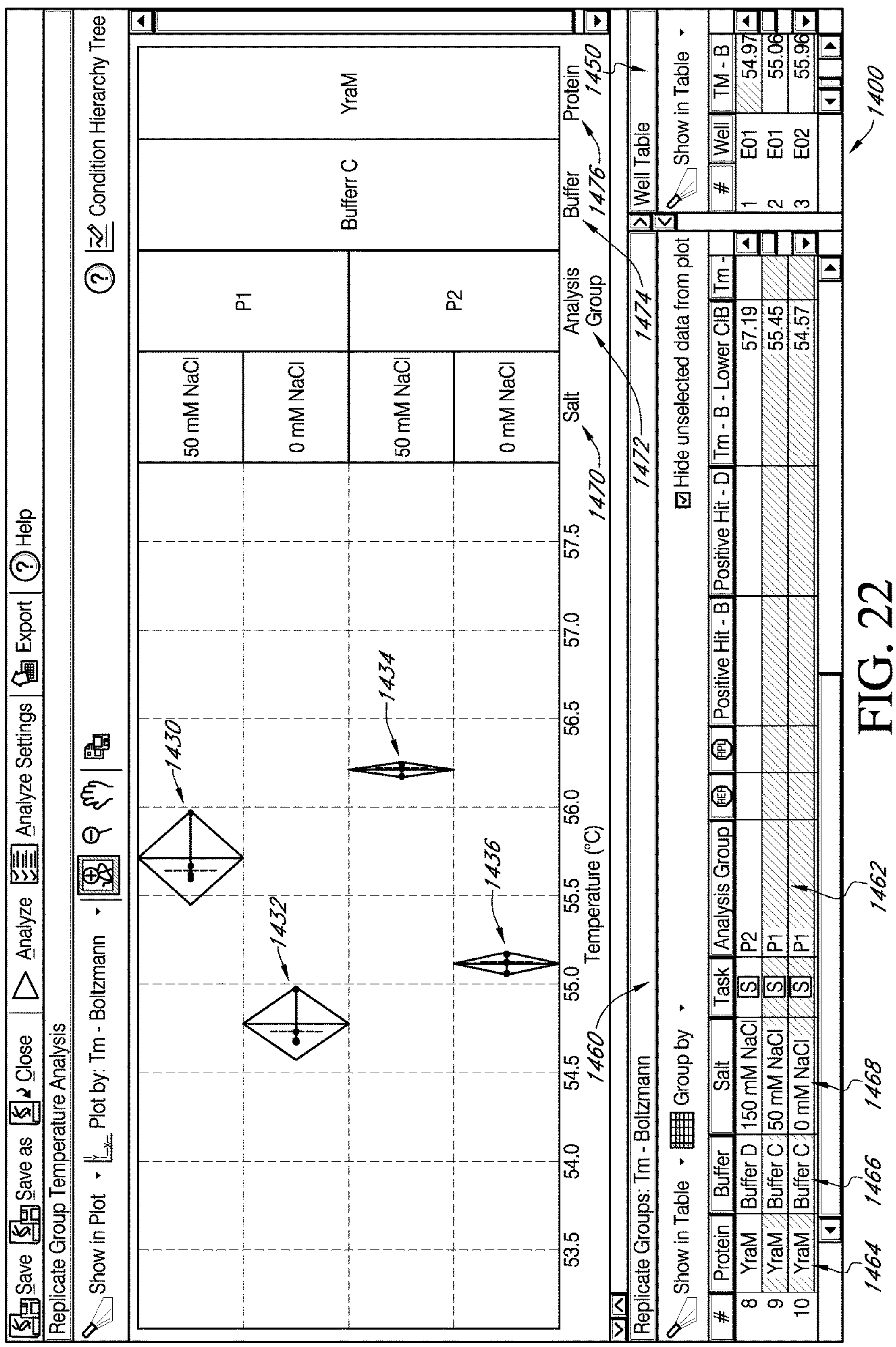
FIG. 22 is an exemplary portion of embodiments of an interactive GUI of FIG. 19, which displays the facility for viewing the effect of various parameters on replicate data groups.
Figure 23:
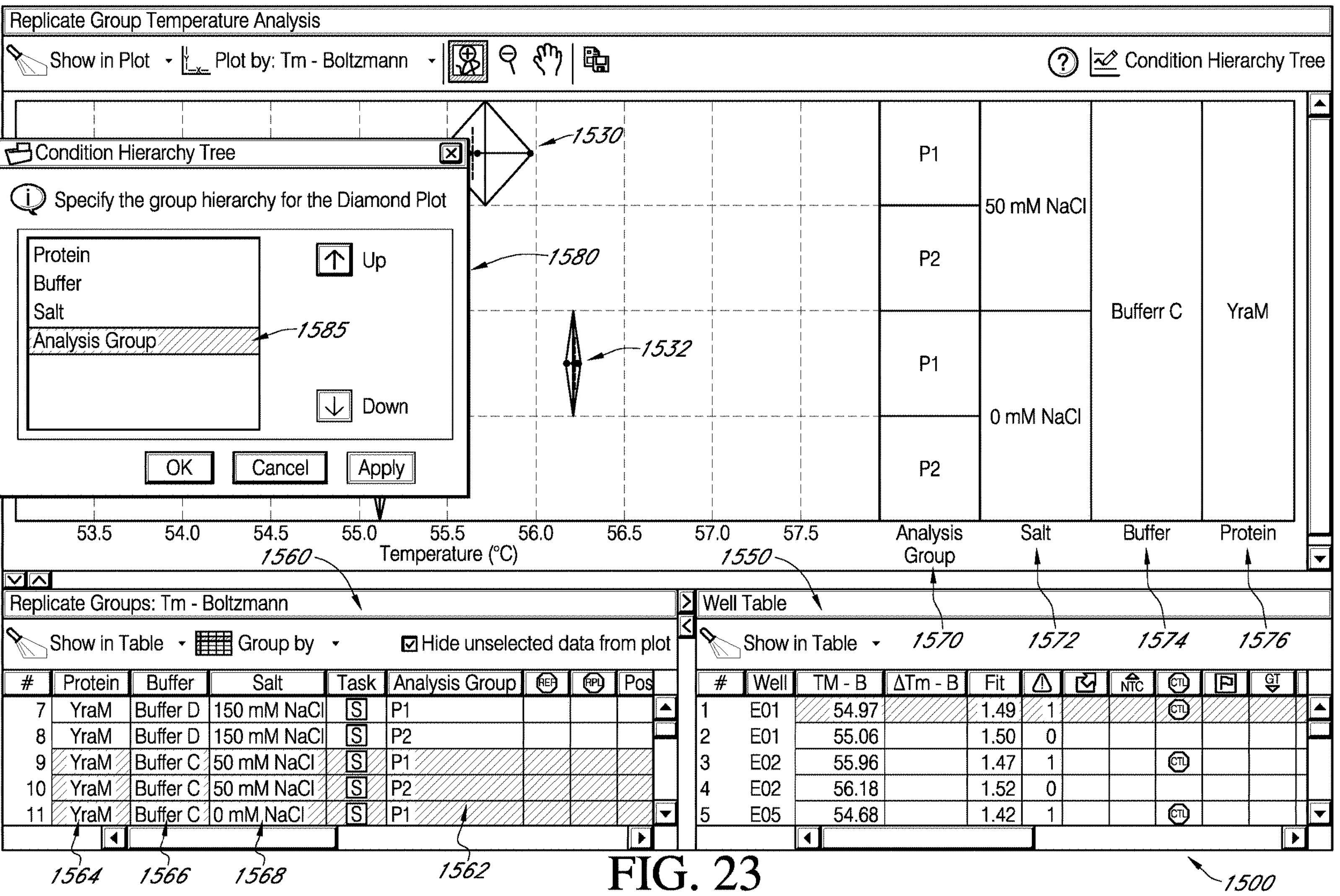
FIG. 23 is an exemplary portion of embodiments of an interactive GUI of FIG. 19, which displays the facility for viewing the effect of various parameters on replicate data groups.

In various embodiments of an interactive GUI according to the present teachings, a popup box may be used to change the order of the variables, and hence the hierarchy. This may allow an end user the ability to sequentially and rapidly change experimental variables and evaluate the impact of the variables on replicates selected from a set of protein melt samples. For example, in FIG. 21 and FIG. 22, such a change is demonstrated. For FIG. 21, various embodiments of an interactive GUI 1300 may have a conditional hierarchy tree popup box 1380, which displays a selection of variables. An end user may select any experimental variable and then move a selected variable 1395 to a new position as shown in conditional hierarchy tree popup box 1390. In FIG. 22, that the buffer has been shifted to another position, so that a new set of diamond plots 1430-1436 may be viewed is clear in comparison to diamond plots 1230-1236 of FIG. 20. The ordering of variables 1470-1476 of FIG. 22 has now been reset versus the ordering of variables 1270-1276 of FIG. 20. In FIG. 23, still another selection of order has been done for 1570-1576 of GUI 1500. It is clear that an end user may readily pick out the shift of diamond plots 1530-1532 as a function of analysis group in comparison to, for example salt concentration, as shown in FIG. 22.

Figure 24A:
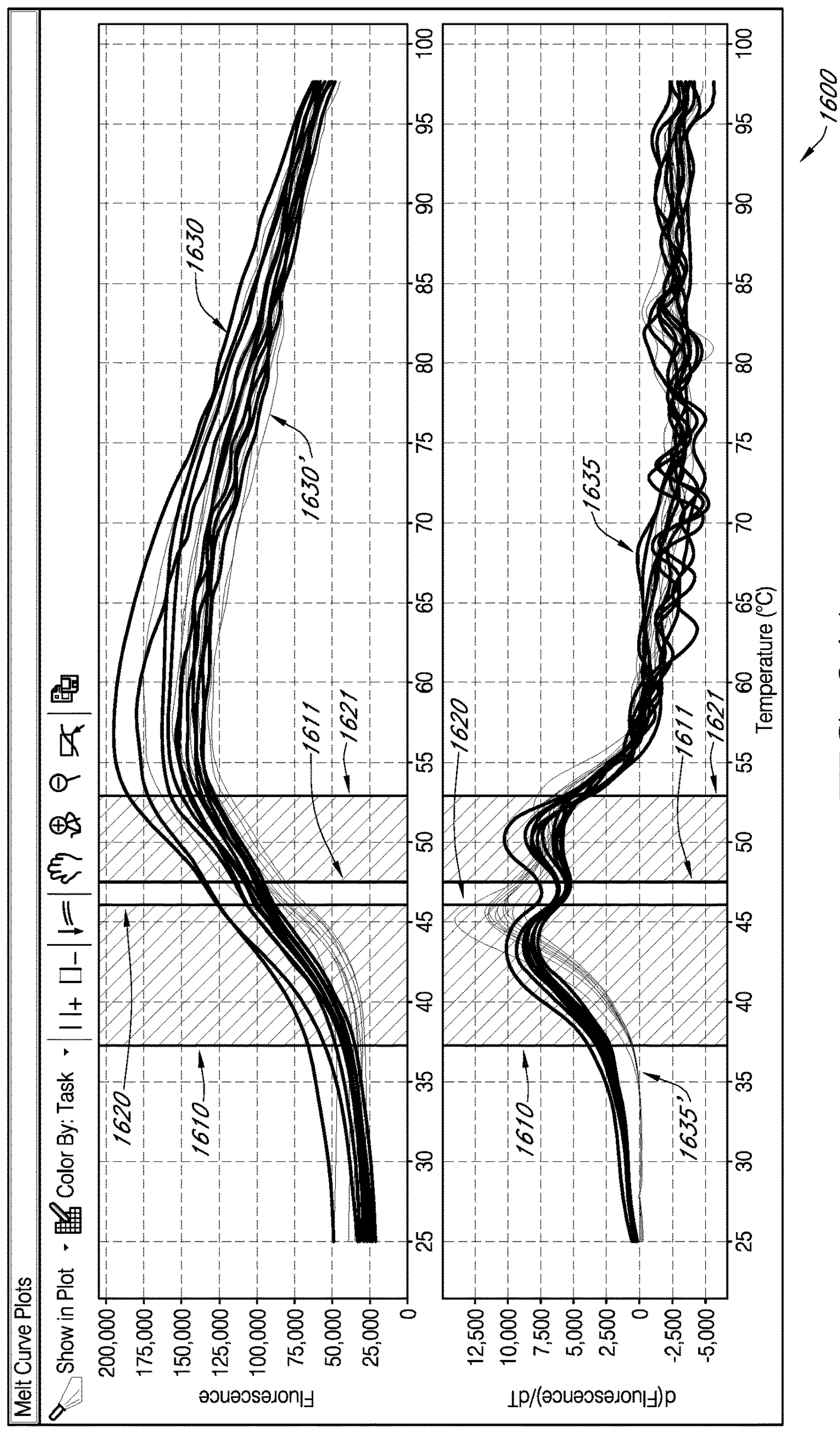
FIG. 24A and FIG. 24B are exemplary portions of embodiments of an interactive GUI of the present teachings, which display the facility for viewing a selected set of data exhibiting biphasic melt.
Figure 24B:
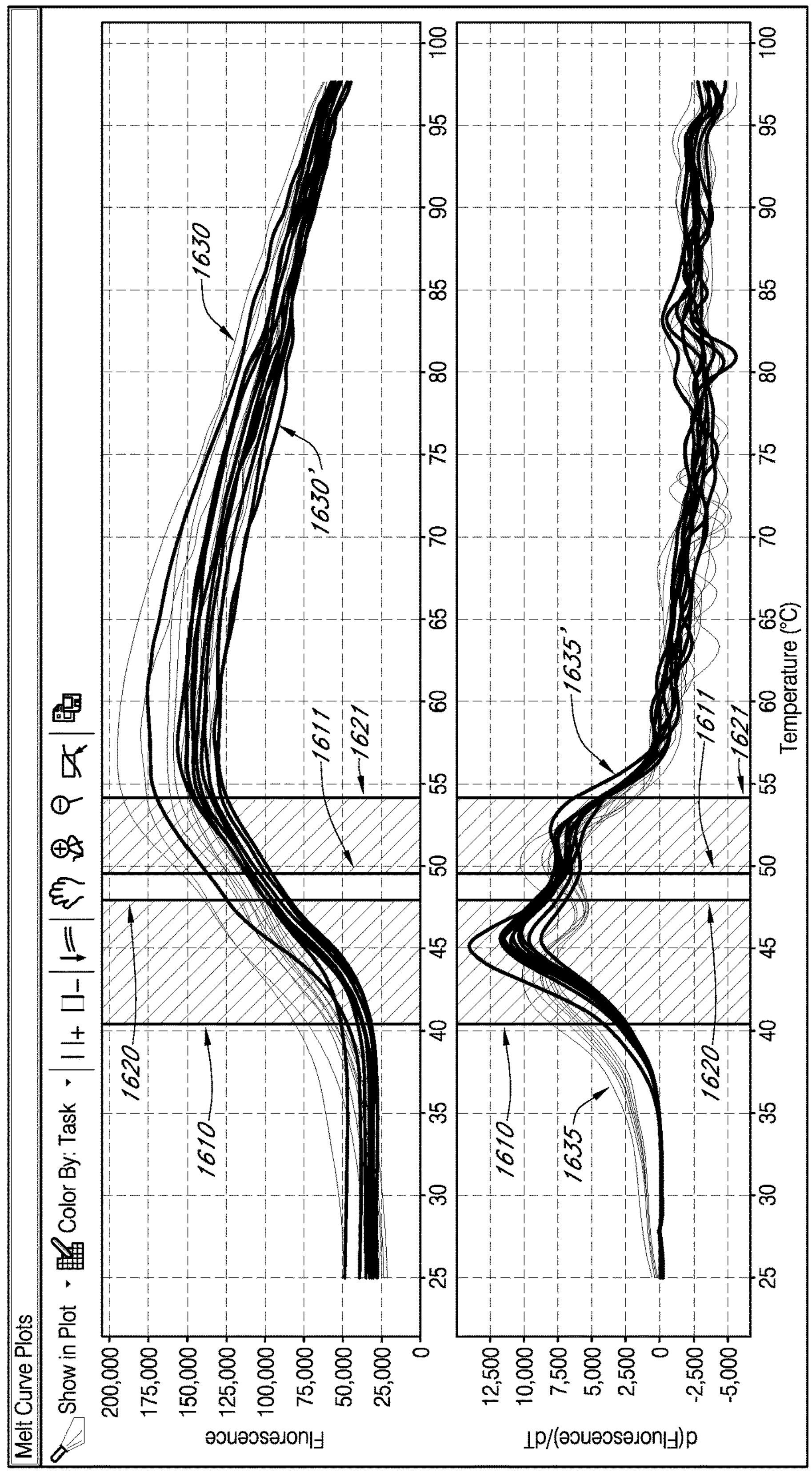
Figure 24C:
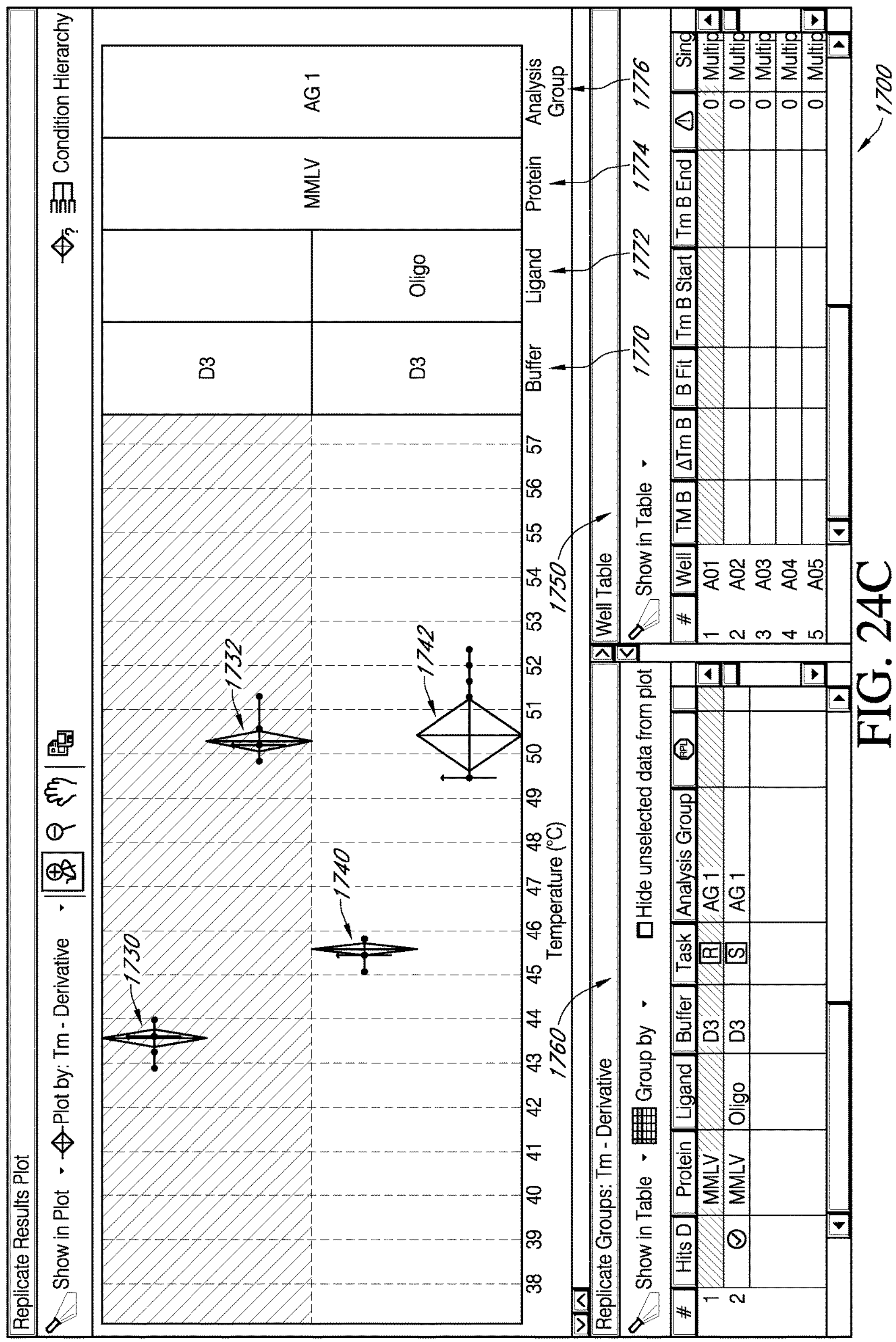
FIG. 24C is an exemplary portion of embodiments of an interactive GUI of the present teachings, which displays the facility for viewing the effect of various parameters on replicate data groups from the data sets selected in FIG. 24A and FIG. 24B.

FIG. 24A-FIG. 24C depict various embodiments of an interactive GUI 1600 displaying processed data for a replicate set of reference and experimental data for a protein having a biphasic melt profile. In FIG. 24A, various embodiments of GUI 1600 may display a first set of protein melt curves 1630 and the corresponding first set of derivative curves 1635. Additionally, various embodiments may provide an end user the selection of an additional set or sets of protein melt curves, such as protein melt curves set 1630' and corresponding set of derivative curves 1635', which may be viewed simultaneously with a first set. In this fashion an end user may dynamically compare sets of data taken, for example, using different experimental conditions, or taken from a different run. For various embodiments of systems and methods for analyzing protein melt curve data, a first curve set may appear visually more distinctly than a selected second set, allowing a focus on interactive analysis of a first set, while maintaining a visual reference to a second set. In FIG. 24A, for example, a first reference set of protein melt curves 1630 and corresponding derivative curves 1635 is more pronounced, than an experimental set of protein melt curves 1630' and corresponding derivative curves 1635'. In comparison in FIG. 24B for GUI 1610, the set of experimental protein melt curves 1630' and corresponding derivative curves 1635' have been selected for analysis by an end user for viewing, and appear more pronounced than the reference set of protein melt curves 1630 and corresponding derivative curves 1635. Additionally, an end user is able to select regions of analysis for the reference set of protein melt curves, as shown in FIG. 24A and FIG. 24B. In FIG. 24A, for example, for the reference set of protein melt curves, a first phase of the protein melt is bounded by a region selected by 1610-1620, while for the second phase of the protein melt, the region bounded by 1611-1621 has been selected.

In FIG. 24C, for various embodiments of an interactive GUI 1700, replicate group statistics are depicted for a protein displaying a biphasic melt, as shown in FIGS. 24A and 24B. In the top view first diamond plot 1730 and second diamond plot 1732 depict the replicate group statistics for the first and second melt phases of a selected curves 1630 as shown in FIG. 24A. In the bottom view first diamond plot 1740 and second diamond plot 1742 depict the replicate group statistics for the first and second melt phases of a selected curves 1630' as shown in FIG. 24B. For example, a ligand may actually shift peaks 1740, 1742 in comparison to a native protein melt 1730-1732. Such a comparison may become readily observable to an end user by using various embodiments of replicate group visualization, according to various embodiments of systems and methods of the present teachings.

Figure 25A:
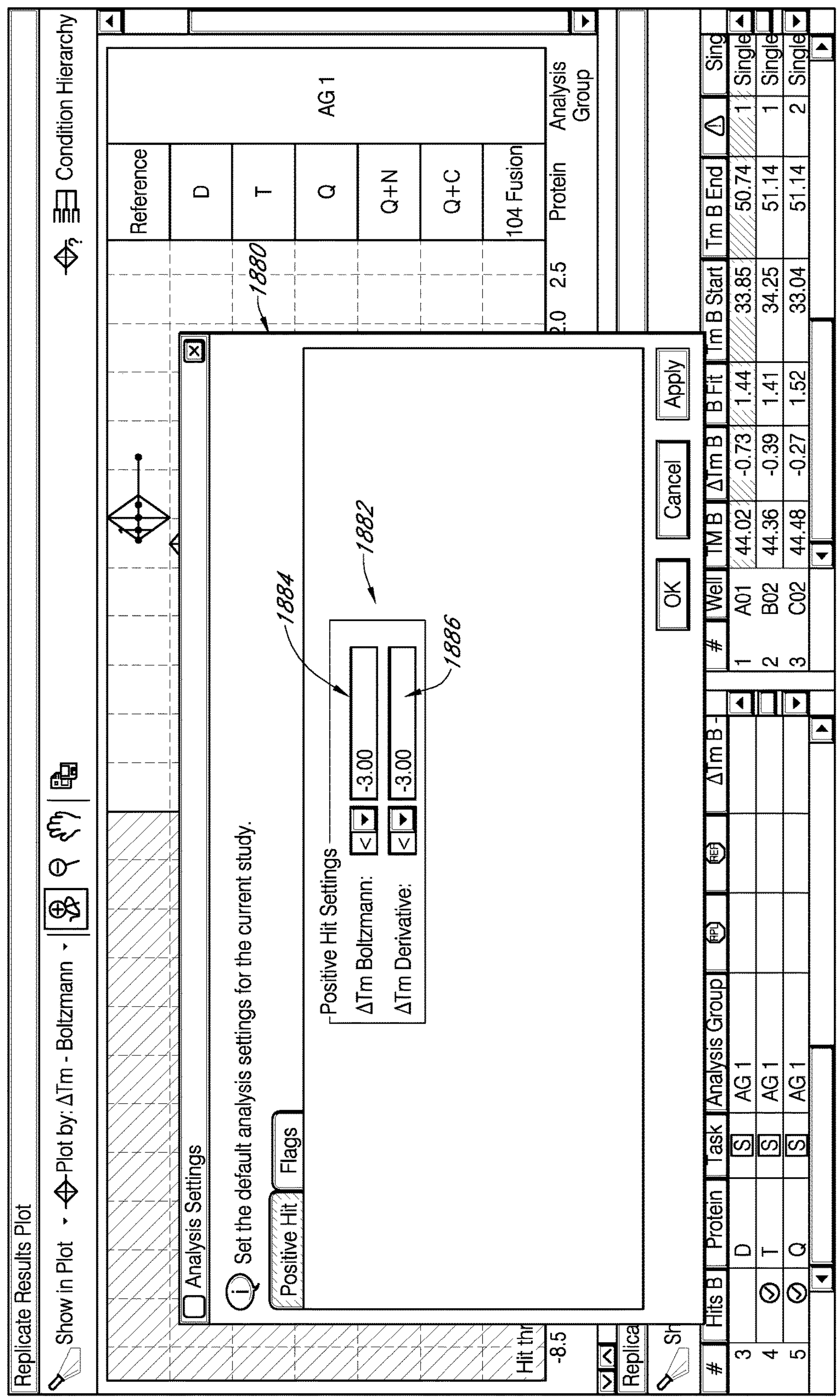
FIG. 25A depicts an exemplary portion of a feature of an interactive GUI according to various embodiments for a system providing protein melt analysis, which displays the facility for viewing results from a selected positive threshold value for $\Delta T_m$ □□via a selection from an exemplary popup window.
Figure 25B:
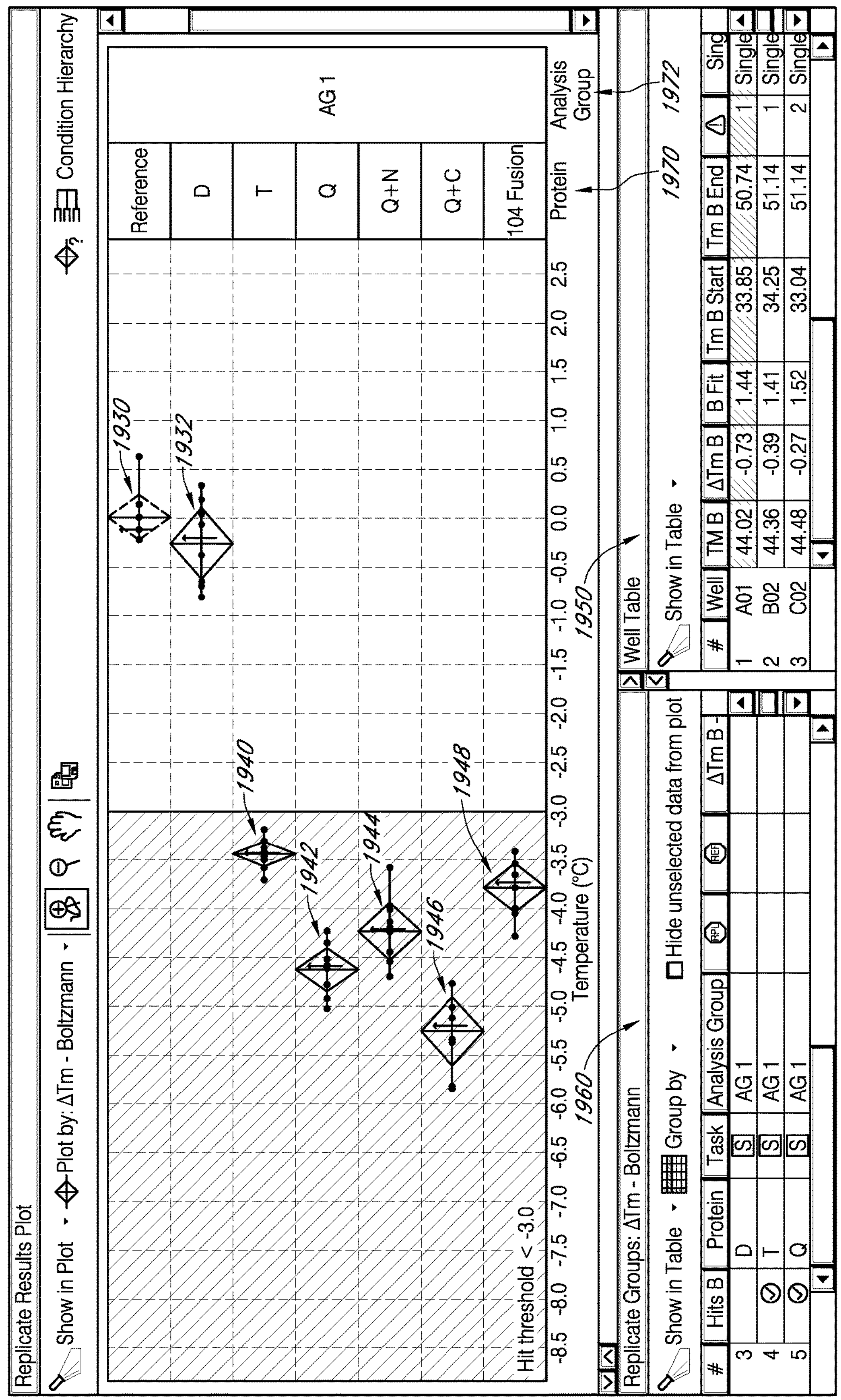
FIG. 25B is an exemplary portion of embodiments of an interactive GUI of FIG. 25A, which displays the facility for viewing replicate data groups falling within the positive threshold selected.

In addition to ready inspection of the impact of experimental variables on a selected group of replicates from a plurality of samples, the diamond plots may be evaluated with respect to an end user defined threshold value. For various embodiments GUI 1800 of FIG. 25A a popup box 1880 may be selected by an end user. According to various embodiments of systems and methods of the present teachings, a positive hits setting box 1882, may allow an end user to select a negative threshold value for $\Delta T_m$ 1884 defined by a method of curve-fitting of the data, as well as to select a negative threshold value for $\Delta T_m$ 1886 defined by an nth order derivative. For example, in GUI 1900 of FIG. 25A, an end user would like to particularly highlight any replicate group have a $T_m$ less than 3 units lower than that of the reference. In GUI 1900 of FIG. 25B, a threshold so selected may allow an end user to see the position of the diamond plots 1940-1948 of groups below the selected threshold of a selected reference. In GUI 1900 of FIG. 25B, a reference diamond plot 1930 is shown. While diamond plots for experimental sets 1940-1948 are highlighted as falling below the selected threshold, the diamond plot 1932 clearly falls outside the selection range. In that regard, diamond plots 1940-1948 are visually highlighted as replicate groups of interest to an end user.

Figure 26A:
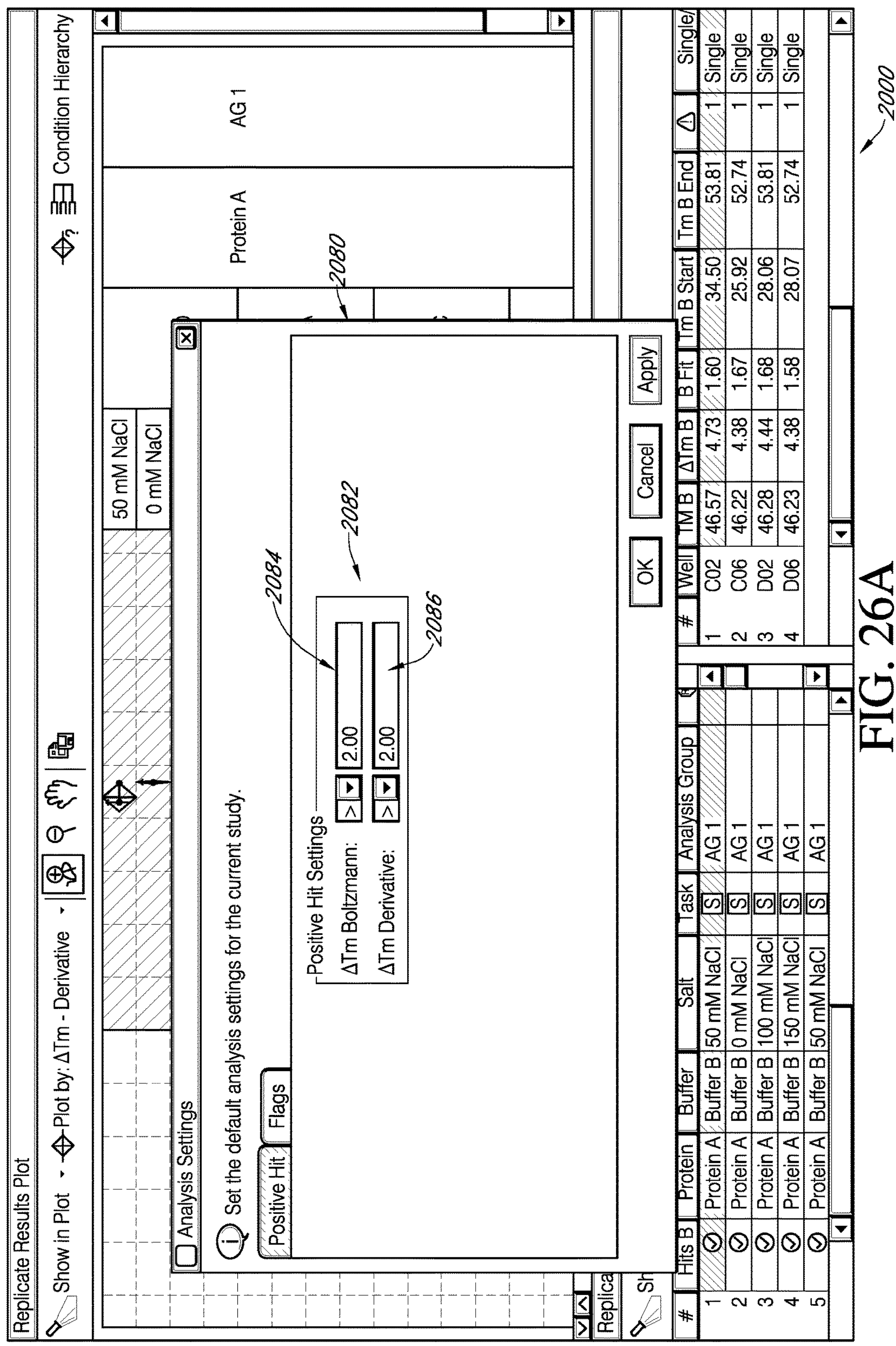
FIG. 26A depicts an exemplary portion of a feature of an interactive GUI according to the present teachings, which displays the facility for viewing results from a selected negative threshold value for $\Delta T_m$ □□via a selection from an exemplary popup window.
Figure 26B:
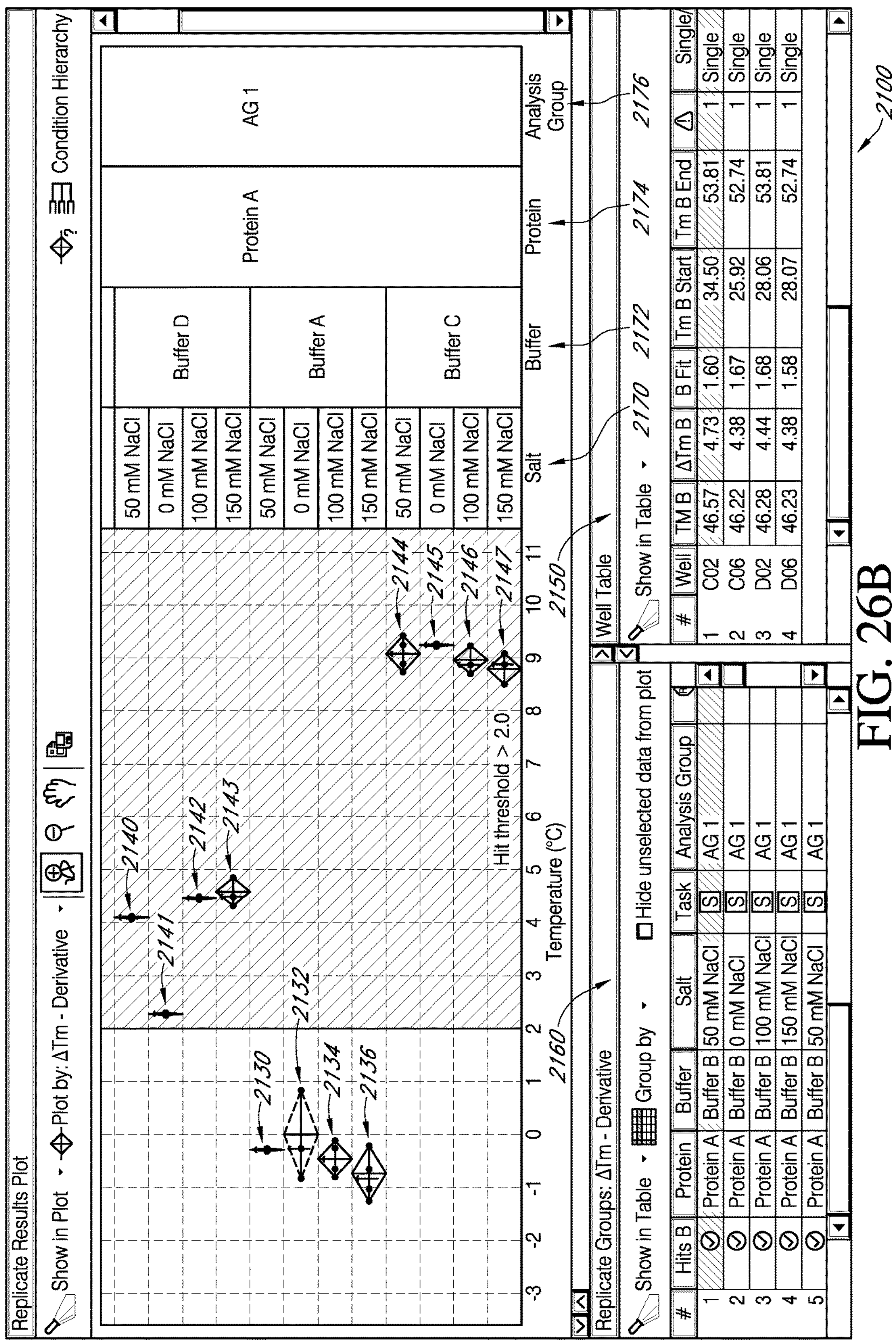
FIG. 26B is an exemplary portion of embodiments of an interactive GUI of FIG. 25A, which displays the facility for viewing replicate data groups falling within the negative threshold selected.

Further, as shown in FIGS. 26A and 26B, an end user may also select a positive threshold value. For various embodiments GUI 2000 of FIG. 26A, a popup box 2080 may be selected by an end user. According to various embodiments of systems and methods of the present teachings, a positive hits setting box 2082, may allow an end user to select a positive threshold value for $\Delta T_m$ 2084 defined by a method of curve-fitting of the data, as well as to select a positive threshold value for $\Delta T_m$ 2086 defined by an nth order derivative. For example, in GUI 2000 of FIG. 26A, an end user would like to particularly highlight any replicate group have a $T_m$ greater than 2 units higher than that of the reference. In GUI 1900 of FIG. 25B, a threshold so selected may allow an end user to see the position of the diamond plots 1940-1948 of groups below the selected threshold of a selected reference. In GUI 2100 of FIG. 26B, a reference diamond plot 2130 is shown. While diamond plots for experimental sets 2140-2147 are highlighted as falling above the selected threshold, the diamond plots 2132-2136 clearly fall outside the selection range. In that regard, diamond plots 2140-2147 are visually highlighted as replicate groups of interest to an end user.

According to various embodiments of an interactive GUI of the present teachings as depicted in FIGS. 25A, 25B, 26A and 26B, such an interactive GUI may readily allow an end user to evaluate whether or not a set of experimental values had a desired impact. For example, if an experiment was designed to see whether or not a set of variables might increase or decrease the $T_m$ values for a selected set of replicates, then a threshold for an expected value may be set, and the diamond plots evaluated against the expected threshold.

Finally, regarding FIG. 4, step 60 as well as FIG. 5 and FIG. 6, step 70, as previously discussed, and as one of ordinary skill in the art may readily recognize, there are various ways of outputting protein melt curve information; for example, but not limited by melt curve plots, $T_m$ values, and $\Delta T_m$ values, to an end user in numerous formats using numerous devices. For example, with respect to format of protein melt curve information, the information may be presented in a graphical format, as a written report, or combinations thereof. With respect to output devices, protein melt curve information may be output to devices such as, but not limited by a printer, a cathode ray tube (CRT) display, a liquid crystal display (LCD), and a light-emitting diode (LED) display.

While the principles of various embodiments of systems and methods for the analysis of protein melt curve data have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A system comprising:

a processor; and a memory in communication with the processor, the memory storing instructions for:

receiving by the processor a set of initial protein melt curve data corresponding to an analysis group, wherein the analysis group comprises sample data from a plurality of sample support devices;

generating and displaying a plurality of melt curves obtained from a first set of processed protein melt curve data from the initial protein melt curve data;

displaying an analysis group window indicating the analysis group to which the initial protein melt curve data corresponds;

presenting a user interface for selecting a temperature range over which a region of the plurality of melt curves extend; and in response to receiving input of a selected temperature range via the interface:

generating a second set of processed protein melt curve data, the second set of protein melt curve data comprising a fit of the first set of processed protein melt curve data over the selected temperature range, and displaying the second set of protein melt curve data as a melt curve.

2. The system of claim 1, wherein the initial protein melt curve data comprises a detector response value as a function of temperature for an end-user selected analysis group.

3. The system of claim 1, wherein the fit is a Boltzmann fit.

4. The system of claim 1, wherein the first set of processed protein melt curve data comprises nth derivatives of the initial protein melt curve data.

5. The system of claim 1, wherein the instructions further comprise generating and displaying a diamond plot displaying replicate group central tendency and variance based on the initial protein melt curve data and the second set of processed protein melt curve data.

6. The system of claim 1, wherein the memory further stores instructions comprising:

in response to receiving a user input via the interface, generating and presenting a data table simultaneously with generating and displaying the second set of processed protein melt curve data.

7. A non-transitory computer-readable medium encoded with instructions, executable by a processor, for analyzing protein melt curve data, the instructions comprising instructions for:

receiving a set of initial protein melt curve data for a plurality of samples from a plurality of sample support devices;

generating and displaying a plurality of melt curves obtained from a first set of processed protein melt curve data from the initial protein melt curve data;

displaying an analysis group window indicating an analysis group to which the initial protein melt curve data corresponds;

presenting a user interface for selecting a temperature range over which a region of the plurality of melt curves extend; and in response to receiving input of a selected temperature range via the interface:

generating a second set of processed protein melt curve data, the second set of protein melt curve data comprising a fit of the first set of processed protein melt curve data over the selected temperature range, and displaying the second set of protein melt curve data as a melt curve.

8. The non-transitory computer-readable medium of claim 7, wherein the initial protein melt curve data comprises a detector response value as a function of temperature for an end-user selected analysis group.

9. The non-transitory computer-readable medium of claim 7, wherein the display of the fit is a Boltzmann fit.

10. The non-transitory computer-readable medium of claim 7, wherein the first set of processed protein melt curve data comprises nth derivatives of the initial protein melt curve data.

11. The non-transitory computer-readable medium of claim 7, wherein the instructions further comprise generating and displaying a diamond plot displaying replicate group central tendency and variance based on the initial protein melt curve data and the second set of processed protein melt curve data.

12. The non-transitory computer-readable medium of claim 7, wherein the instructions further comprise:

in response to receiving a user input via the interface, generating and presenting a data table simultaneously with generating and displaying the second set of processed protein melt curve data.

13. A computer implemented method for determining a genotype for a genomic locus in a biological sample, the method comprising:

receiving by a processor a set of initial protein melt curve data corresponding to an analysis group, wherein the analysis group comprises sample data from a plurality of sample support devices;

processing the set of initial protein melt curve data on a computer, the processing comprising:

generating and displaying a plurality of melt curves obtained from a first set of processed protein melt curve data from the initial protein melt curve data;

displaying an analysis group window indicating the analysis group to which the initial protein melt curve data corresponds;

presenting a user interface for selecting a temperature range over which a region of the plurality of melt curves extend; and in response to receiving input of a selected temperature range via the interface:

generating a second set of processed protein melt curve data, the second set of protein melt curve data comprising a fit of the first set of processed protein melt curve data over the selected temperature range, and displaying the second set of protein melt curve data as a melt curve.

14. The computer implemented method of claim 13, wherein the initial protein melt curve data comprises a detector response value as a function of temperature for an end-user selected analysis group.

15. The computer implemented method of claim 13, wherein the fit is a Boltzmann fit.

16. The computer implemented method of claim 13, wherein the first set of processed protein melt curve data comprises nth derivatives of the initial protein melt curve data.

17. The computer implemented method of claim 13, further comprising generating and displaying a diamond plot displaying replicate group central tendency and variance based on the initial protein melt curve data and the second set of processed protein melt curve data.

18. The computer implemented method of claim 13, further comprising:

in response to receiving a user input via the interface, generating and presenting a data table simultaneously with generating and displaying the second set of processed protein melt curve data.

* * * * *